United States Patent
Valia et al.

(10) Patent No.: US 9,713,585 B2
(45) Date of Patent: Jul. 25, 2017

(54) NAIL COATINGS HAVING ENHANCED ADHESION

(71) Applicant: Creative Nail Design, Inc., Vista, CA (US)

(72) Inventors: David Valia, San Diego, CA (US); Jamie Ellis, Vista, CA (US)

(73) Assignee: CREATIVE NAIL DESIGN, INC., Vista, CA (US)

( * ) Notice: Subject to any disclaimer, the term of this patent is extended or adjusted under 35 U.S.C. 154(b) by 0 days.

(21) Appl. No.: 14/786,491

(22) PCT Filed: Apr. 22, 2014

(86) PCT No.: PCT/US2014/035028
§ 371 (c)(1),
(2) Date: Oct. 22, 2015

(87) PCT Pub. No.: WO2014/176275
PCT Pub. Date: Oct. 30, 2014

(65) Prior Publication Data
US 2016/0067164 A1 Mar. 10, 2016

Related U.S. Application Data

(60) Provisional application No. 61/814,691, filed on Apr. 22, 2013.

(51) Int. Cl.
| | | |
|---|---|---|
| A61K 8/00 | (2006.01) | |
| A61K 8/58 | (2006.01) | |
| A61Q 3/02 | (2006.01) | |
| A61K 8/81 | (2006.01) | |
| A61K 8/31 | (2006.01) | |
| A61K 8/35 | (2006.01) | |
| A61K 8/37 | (2006.01) | |
| A61K 8/49 | (2006.01) | |
| A61K 8/73 | (2006.01) | |
| A61K 8/85 | (2006.01) | |
| A61K 8/86 | (2006.01) | |

(52) U.S. Cl.
CPC ............... *A61K 8/585* (2013.01); *A61K 8/31* (2013.01); *A61K 8/35* (2013.01); *A61K 8/37* (2013.01); *A61K 8/4973* (2013.01); *A61K 8/731* (2013.01); *A61K 8/8152* (2013.01); *A61K 8/85* (2013.01); *A61K 8/86* (2013.01); *A61Q 3/02* (2013.01); *A61K 2800/592* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 2,465,188 A | | 3/1949 | Barry et al. |
| 4,871,534 A | | 10/1989 | Montgomery |
| 5,047,492 A | | 9/1991 | Weidner et al. |
| 5,130,125 A | | 7/1992 | Martin et al. |
| 5,302,379 A | | 4/1994 | Sojka |
| 5,356,616 A | * | 10/1994 | Sojka ..................... A61Q 3/02 424/61 |
| 5,389,726 A | | 2/1995 | Sojka |
| 5,484,867 A | | 1/1996 | Lichtenhan et al. |
| 5,512,272 A | | 4/1996 | Krzysik |
| 5,512,273 A | | 4/1996 | Martin |
| 5,576,509 A | | 11/1996 | Refouvelet et al. |
| 5,589,562 A | | 12/1996 | Lichtenhan et al. |
| 5,639,447 A | | 6/1997 | Patel |
| 5,643,555 A | | 7/1997 | Collin et al. |
| 5,662,891 A | | 9/1997 | Martin |
| 5,676,938 A | | 10/1997 | Kimura et al. |
| 5,720,804 A | | 2/1998 | Martin |
| 5,750,741 A | | 5/1998 | Crocker et al. |
| 5,785,958 A | | 7/1998 | Sirdesai et al. |
| 5,858,544 A | | 1/1999 | Banaszak Holl et al. |
| 5,939,576 A | | 8/1999 | Lichtenhan et al. |
| 5,942,638 A | | 8/1999 | Lichtenhan et al. |
| 5,965,147 A | | 10/1999 | Steffier |
| 5,985,951 A | | 11/1999 | Cook |
| 6,051,242 A | | 4/2000 | Patel et al. |
| 6,100,417 A | | 8/2000 | Lichtenhan et al. |
| 6,127,557 A | | 10/2000 | Van Santen et al. |
| 6,207,364 B1 | | 3/2001 | Takamuki et al. |

(Continued)

FOREIGN PATENT DOCUMENTS

| | | |
|---|---|---|
| EP | 0 432 572 A2 | 6/1991 |
| FR | 2 939 661 A1 | 6/2010 |

(Continued)

OTHER PUBLICATIONS

Ayandele et al. Polyhedral Oligomeric Silsesquioxane (POSS)—Containing Polymer Nanocomposites (review). Nanomaterials 2012, 2, 445-475.*
EP0409_Product Information by Hibrid the creators of POSS. 2015. 1 page.*
EP0408_Product Information by Hibrid the creators of POSS. 2015. 1 page.*
U.S. Appl. No. 61/692,096, filed Aug. 22, 2012, Valia et al.
International Search Report of International Application No. PCT/US2014/035028 filed on Apr. 22, 2014.
International Search Report and Written Opinion dated Nov. 12, 2014, issued in International Application No. PCT/US2013/035798.

(Continued)

*Primary Examiner* — Robert A Wax
*Assistant Examiner* — Olga V Tcherkasskaya
(74) *Attorney, Agent, or Firm* — Venable LLP; Keith G. Haddaway

(57) ABSTRACT

Adhesion of a composition for nail coatings be improved by addition of a polyhedral oligomeric silsesquioxane (POSS). Nail coating compositions that benefit from the addition of a POSS include enamels, reactive composition such as those containing acrylates, solventless compositions and water-based compositions.

15 Claims, No Drawings

(56) References Cited

U.S. PATENT DOCUMENTS

| | | |
|---|---|---|
| 6,252,030 B1 | 6/2001 | Zank et al. |
| 6,254,878 B1 | 7/2001 | Bednarek et al. |
| 6,270,561 B1 | 8/2001 | Nguyen |
| 6,277,451 B1 | 8/2001 | Mehl et al. |
| 6,280,756 B1 | 8/2001 | Ramin et al. |
| 6,362,279 B2 | 3/2002 | Lichtenhan et al. |
| 6,372,843 B1 | 4/2002 | Barruel et al. |
| 6,425,936 B1 | 7/2002 | Sammons et al. |
| 6,486,254 B1 | 11/2002 | Barbee et al. |
| 6,489,079 B1 | 12/2002 | Verschueren et al. |
| 6,653,365 B2 | 11/2003 | Jia |
| 6,716,919 B2 | 4/2004 | Lichtenhan et al. |
| 6,759,460 B2 | 7/2004 | Kamo et al. |
| 6,818,207 B1 | 11/2004 | Schoon et al. |
| 6,927,270 B2 | 8/2005 | Lichtenhan et al. |
| 6,939,551 B2 | 9/2005 | Amato et al. |
| 6,991,782 B2 | 1/2006 | Kanji et al. |
| 7,011,821 B2 | 3/2006 | Amato et al. |
| 7,198,639 B2 | 4/2007 | Lai et al. |
| 7,297,460 B2 | 11/2007 | Vanmaele et al. |
| 7,320,956 B2 | 1/2008 | Johnson et al. |
| 7,572,872 B2 | 8/2009 | Flodin et al. |
| 7,678,321 B2 | 3/2010 | Sirdesai et al. |
| 7,682,622 B2 | 3/2010 | Horino |
| 7,704,517 B2 | 4/2010 | Wang et al. |
| 7,722,899 B2 | 5/2010 | Ono et al. |
| 7,723,415 B2 | 5/2010 | Lichtenhan et al. |
| 7,786,209 B2 | 8/2010 | Carlini et al. |
| 7,803,358 B2 | 9/2010 | Gordan et al. |
| 7,829,073 B2 | 11/2010 | Martin et al. |
| 7,879,316 B2 | 2/2011 | Ferrari et al. |
| 7,943,120 B2 | 5/2011 | Toyoda et al. |
| 7,964,747 B2 | 6/2011 | Kim et al. |
| 7,985,523 B2 | 7/2011 | Zhou et al. |
| 8,025,869 B2 | 9/2011 | Yu |
| 1,026,237 A1 | 10/2011 | Hinterman et al. |
| 8,084,177 B2 | 12/2011 | Zhou et al. |
| 8,124,058 B2 | 2/2012 | Schoon et al. |
| 8,133,478 B2 | 3/2012 | Maitra et al. |
| 8,263,677 B2 | 9/2012 | Conger et al. |
| 8,367,742 B2 | 2/2013 | Vu et al. |
| 8,399,537 B2 | 3/2013 | Conger et al. |
| 8,637,585 B2 * | 1/2014 | Frey .................... C07F 7/21 |
| | | 522/148 |
| 2002/0114773 A1 | 8/2002 | Kanji et al. |
| 2003/0012750 A1 | 1/2003 | Socci et al. |
| 2004/0120915 A1 | 6/2004 | Yang et al. |
| 2004/0180011 A1 | 9/2004 | Schlosser |
| 2004/0191201 A1 | 9/2004 | Maio et al. |
| 2004/0202622 A1 | 10/2004 | Quadir |
| 2004/0202623 A1 | 10/2004 | Quadir |
| 2005/0065297 A1 | 3/2005 | Patel |
| 2005/0142089 A1 | 6/2005 | Lu et al. |
| 2005/0201961 A1 | 9/2005 | Lu et al. |
| 2005/0220745 A1 | 10/2005 | Lu |
| 2005/0244351 A1 | 11/2005 | Reinhart et al. |
| 2006/0008441 A1 | 1/2006 | Kanji et al. |
| 2006/0110346 A1 | 5/2006 | Lu |
| 2006/0263318 A1 | 11/2006 | Lichtenhan et al. |
| 2007/0132113 A1 | 6/2007 | Hinterman |
| 2007/0141008 A1 | 6/2007 | Jones |
| 2007/0166271 A1 | 7/2007 | Gordon et al. |
| 2007/0286827 A1 | 12/2007 | Sheariss et al. |
| 2008/0081022 A1 * | 4/2008 | Yu .................... A61K 8/585 |
| | | 424/43 |
| 2008/0102050 A1 | 5/2008 | Li et al. |
| 2008/0175804 A1 | 7/2008 | Farcet |
| 2008/0181859 A1 | 7/2008 | Farcet |
| 2008/0305062 A1 | 12/2008 | Bui et al. |
| 2009/0087473 A1 | 4/2009 | Inage |
| 2009/0233031 A1 | 9/2009 | Weber et al. |
| 2010/0012263 A1 | 1/2010 | Oshima et al. |
| 2010/0055061 A1 | 3/2010 | Mandelli et al. |
| 2010/0074854 A1 | 3/2010 | Guerchet et al. |
| 2010/0098761 A1 | 4/2010 | Song et al. |
| 2010/0166685 A1 | 7/2010 | Farcet |
| 2011/0020413 A1 | 1/2011 | Gormley et al. |
| 2011/0042004 A1 | 2/2011 | Schubert et al. |
| 2011/0081306 A1 | 4/2011 | Vu et al. |
| 2011/0082228 A1 | 4/2011 | Vu |
| 2011/0110994 A1 | 5/2011 | Inokuchi et al. |
| 2011/0236341 A1 | 9/2011 | Dop |
| 2011/0274633 A1 | 11/2011 | Vu et al. |
| 2012/0003167 A1 | 1/2012 | Cavazzuti et al. |
| 2012/0014899 A1 | 1/2012 | Dop |
| 2012/0064019 A1 | 3/2012 | Cavazzuti et al. |
| 2012/0100089 A1 | 4/2012 | Barba et al. |
| 2012/0128746 A1 | 5/2012 | Maitra et al. |
| 2012/0142793 A1 * | 6/2012 | Frey .................... C07F 7/21 |
| | | 521/50.5 |
| 2012/0171137 A1 | 7/2012 | Bradsaw et al. |
| 2012/0172495 A1 * | 7/2012 | Czubarow ............ C08G 59/306 |
| | | 523/456 |
| 2014/0053859 A1 | 2/2014 | Valia et al. |
| 2014/0056833 A1 | 2/2014 | Vu et al. |

FOREIGN PATENT DOCUMENTS

| | | |
|---|---|---|
| WO | WO-9848769 A1 | 11/1998 |
| WO | WO-2011/011304 A2 | 1/2011 |
| WO | WO-2011/031578 A1 | 3/2011 |
| WO | WO-2011/043879 A1 | 4/2011 |
| WO | WO-2011/043880 A1 | 4/2011 |
| WO | WO-2012018403 A1 | 2/2012 |
| WO | WO-2012078751 A2 | 6/2012 |
| WO | WO-2012089692 A2 | 7/2012 |

OTHER PUBLICATIONS

International Search Report and Written Opinion dated Sep. 9, 2014, issued in International Application No. PCT/US2014/035028.

* cited by examiner

NAIL COATINGS HAVING ENHANCED ADHESION

CLAIM OF PRIORITY

This application is a U.S. National Stage of International Application No. PCT/US2014/035028, filed on Apr. 22, 2014, which claims priority to U.S. Provisional Application No. 61/814,691, filed Apr. 22, 2013, which is incorporated by reference in its entirety.

TECHNICAL FIELD

Embodiments of the present disclosure relate to nail coatings. In particular, the disclosure relates to nail coating compositions containing at least one polyhedral oligomeric silsesquioxane (POSS) and having improved adhesion.

BACKGROUND

The nail plate (i.e., the natural nail) is primarily composed of keratin, a water-insoluble, fibrous protein that is a major structural component of skin, hair, wool, silk, feathers, scales, nails and hooves. While keratins can obviously differ greatly in their amino acid makeup, hard keratins may all be generally characterized as cross-linked polypeptides. Alpha-keratins such as nails and hooves may be further characterized by their relatively higher percentages of the amino acid cysteine. Typically, the alpha-helix coils of the polypeptides are cross-linked with disulphide bonds between adjacent cysteines. The resulting plate-like cells are cemented to each other with a sticky substance and held together by rivet-like structures called desmosomes. Many cell layers adhere to each other to form the nail plate, a structure that resembles a brick and mortar wall.

Conventional coatings for natural nails may be generally classified into three categories: nail polishes (also known as lacquers, varnish or enamels), artificial nails (also known as gels or acrylics) and hybrids. Nail enamels typically comprise various solid components which are dissolved and/or suspended in non-reactive solvents. Upon application and drying, the solids deposit on the nail surface as a clear, translucent or colored film. Typically, nail polishes are easily scratched and are easily removable with solvent, usually within one minute and if not removed as described, will chip or peel from the natural nail in one to five days.

Nail enamels coat the surface of the nail plate to provide a decorative finish with a characteristic glossy finish. Nail enamels conventionally comprise a film forming component, which is frequently nitrocellulose, cellulose acetate butyrate, or a combination of one or both of those cellulosics with a polyester or other polymeric compound. Most nail polishes are made of nitrocellulose dissolved in a solvent (e.g. butyl acetate or ethyl acetate) and either left clear or colored with various pigments. Typical components may include: film forming agents, resins and plasticizers, solvents, and coloring agents.

Artificial nails polymerize on the surface of a natural nail to form a hard, tough surface. Artificial nails conventionally include one or more (meth)acrylate monomers and a photoinitiator or hardener which may be mixed immediately before use. Optionally, the artificial nail composition may include a solvent or may utilize a liquid (meth)acrylate as a solvent. Artificial nails of this sort typically bond tightly and possibly irreversibly to the nail plate and must be removed by physical means such as filing.

Hybrid systems include both film-forming components and polymerizable components. In exemplary hybrid systems, the polymerizable components, for example (meth)acrylates, form a 3-dimentional (3-D) thermoset lattice and the film forming component, for example nitrocellulose or cellulose acetate butyrate is dispersed within the 3-D network. The 3-D thermoset lattice provides enhanced durability, toughness, and scratch-resistance over conventional nail enamels while the interdispered film-forming component provides a soluble network to allow for improved removability characteristics over artificial nails.

Application of nail coatings to the surface of the nail plate typically requires the surface of the nail plate to be treated. The surface treatment typically involves the use of a primer and/or roughening of the nail plate such as with the use of a file. This treatment process may cause damage to the nail plate, which is particularly problematic for individuals having thin nails.

Primers are adhesion promoters that improve adhesion by increasing interfacial compatibility between surfaces, e.g., the nail plate and an applied coating. For example, a coating of nail polish may resist chipping and peeling if a good primer is used. Primers are more compatible with the nail plate than the nail polish. Primers act as the "go-between" or "anchor", to improve adhesion.

Primers are also frequently used with artificial nail enhancements since acrylic nail products normally have poor adhesion to nail plates. In general, nail plate primers can be thought of as double-sided sticky tape, joining the nail plate to the nail enhancement. The nail plate surface is made up of chemical groups possessing specific structures. Primer components must interact with the nail plate and the (meth)acrylic monomers in the enhancement. With these types of primers, physical abrasion of the nail plate is required to achieve proper levels of adhesion to the keratin substrate. Moreover, these primers can be destructive, and if used improperly they can cause damage to the nail plate and surrounding tissue. These primers can also cause discoloration of the nail enhancement.

There remains a need in the art for nail coatings with enhanced adhesion that do not peel or chip from the nail surface but do not damage or discolor the nail surface.

Throughout this description, including the foregoing description of related art, any and all publicly available documents described herein, including any and all U.S. patents, are specifically incorporated by reference herein in their entirety. The foregoing description of related art is not intended in any way as an admission that any of the documents described therein, including pending United States patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

SUMMARY

The nail coatings described herein provide enhanced adhesion of the coating to the nail, and/or between layers of a multilayer coating.

In one aspect, a nail coating composition includes at least one polyhedral oligomeric silsesquioxane.

The nail coating composition can further include a film-forming polymer. The film-forming polymer can be water-dispersible, and the composition can further include water. The nail coating composition can further include a non-aqueous, non-reactive solvent. The nail coating composition can further include at least one reactive (meth)acrylate; and at least one non-reactive, solvent dissolvable polymer.

The nail coating composition can further include at least one reactive (meth)acrylate; at least one reactive urethane (meth)acrylate; at least one polymethylmethacrylate (PMMA)-polymethylacrylic acid (PMAA) copolymer; at least one non-reactive, solvent dissolvable polymer; and at least one non-reactive solvent. The nail coating composition can further include at least one reactive polypropylene glycol (meth)acrylated monomer or polyethylene glycol (meth)acrylated monomer.

The nail coating composition can further include at least one reactive (meth)acrylate; and a polymerization accelerator, a polymerization initiator, or a combination thereof; wherein the composition is free of added solvent. The nail coating composition can further include a multicarbonyl-vinyl containing monomer.

The nail coating composition can further include at least one reactive urethane (meth)acrylate. The nail coating composition can further include at least one polymethylmethacrylate (PMMA)-polymethylacrylic acid (PMAA) copolymer. The nail coating composition cures to an acrylic thermoset having voids defined therein upon exposure to actinic radiation. The nail coating composition can further include a non-reactive solvent.

The at least one reactive (meth)acrylate can include hydroxypropyl methacrylate (HPMA), hydroxyethyl methacrylate (HEMA), ethyl methacrylate (EMA), tetrahydrofurfuryl methacrylate, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate,1,3-glycerol dimethacrylate/succinate adduct, phthalic acid monoethyl methacrylate, or a mixture thereof.

The nail coating composition can further include at least one reactive polypropylene glycol (meth)acrylated monomer or polyethylene glycol (meth)acrylated monomer.

The nail coating composition can further include an adhesion promoter selected from the group consisting of:
hydroxypropyl methacrylate (HPMA),
hydroxyethyl methacrylate (HEMA),
ethyl methacrylate (EMA),
tetrahydrofurfuryl methacrylate (THFMA),
pyromellitic dianhydride di(meth)acrylate,
pyromellitic dianhydride glyceryl dimethacrylate,
pyromellitic dimethacrylate,
methacroyloxyethyl maleate,
2-hydroxyethyl methacrylate/succinate,
1,3-glycerol dimethacrylate/succinate adduct,
phthalic acid monoethyl methacrylate,
methacroyloxyethyl maleate,
2-hydroxyethyl methacrylate/succinate,
1,3-glycerol dimethacrylate/succinate adduct,
butyl methacrylate,
isobutyl methacrylate,
PEG-4 dimethacrylate,
PPG monomethacrylate,
trimethylolpropane trimethacrylate,
isopropylidenediphenyl bisglycidyl methacrylate,
lauryl methacrylate,
cyclohexyl methacrylate,
hexyl methacrylate,
urethane methacrylate,
triethylene glycol dimethacrylate,
ethylene glycol dimethacrylate,
tetraethylene glycol dimethacrylate,
trimethylolpropane trimethacrylate,
neopentylglycol dimethacylate,
acetoacetoxy methacrylate,
acetoacetoxyethyl methacrylate (AAEMA),
polyetheramine,
glycidyl methacrylates,
maleic anhydride,
terpolymers containing vinyl acetate,
organosilanes,
organotitanates,
chlorinated polyolefins,
sucrose acetate isobutyrate,
caprylic/capric triglyceride,
glyceryl hydrogenated rosinate,
pentaerythryl hydrogenated rosinate,
styrene/methyl styrene/indene copolymer,
blocked isocyanate PVC,
polyamidoamine PVC, and
a mixture thereof.

The at least one polyhedral oligomeric silsesquioxane can include Glycidyl POSS® Cage Mixture (sold by Hybrid Plastics as EP0409); Trimethoxy-[2-(7-oxabicyclo[4.1.0] hept-3-yl)ethyl]silane, hydrolyzed (sold by Hybrid Plastics as EP0408); Hydrolyzed [3-(Trimethoxysilyl)propyl]aniline (sold by Hybrid Plastics as AM0281); [(dimethyl(norbornenylethyl)silyloxy)dihydroxy]-POSS® ((sold by Hybrid Plastics as NB1038); vinyl silsesquioxane resin-liquid (sold by Hybrid Plastics as PM1285MV); Acrylo POSS® Cage Mixture (sold by Hybrid Plastics as MA0736); methacrylated ethoxylated POSS®; ethoxylated glycidyl POSS®; or a mixture thereof.

The nail coating composition can further include a di-, tri-, or poly-functional ethylenically unsaturated reactant.

The solvent-dissolvable polymer or film-forming polymer can be selected from the group consisting of: a cellulose ester, a cellulose acetate alkylate, a cellulose acetate butyrate, a cellulose acetate propionate, ethyl tosylamide, adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, poly lactic acid, nitrocellulose, cellulose ester, and mixtures thereof.

In another aspect, a method of improving adhesion of a nail coating comprising adding at least one polyhedral oligomeric silsesquioxane to the nail coating composition.

In the method, the nail coating composition can further include at least one reactive (meth)acrylate; and at least one non-reactive, solvent dissolvable polymer. The nail coating composition can further include: at least one reactive (meth) acrylate; at least one reactive urethane (meth)acrylate; at least one polymethylmethacrylate (PMMA)-polymethylacrylic acid (PMAA) copolymer; at least one non-reactive, solvent dissolvable polymer; and at least one non-reactive solvent. The nail coating composition can further include at least one reactive polypropylene glycol (meth)acrylated monomer or polyethylene glycol (meth)acrylated monomer.

In the method the nail coating composition can further include a film-forming polymer. The film-forming polymer can be water-dispersible, and the composition can further include water.

The nail coating composition can further include a non-aqueous, non-reactive solvent. The nail coating composition can further include: at least one reactive (meth)acrylate; a polymerization accelerator, a polymerization initiator, or a combination thereof; and wherein the composition is free of added solvent. The nail coating composition can further include a multicarbonyl-vinyl containing monomer.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the description is to be regarded as illustrative in nature and not as restrictive.

DETAILED DESCRIPTION

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural references unless the context clearly dictates otherwise. Thus, for example, a reference to "a composition" includes a plurality of such compositions, as well as a single composition.

The terms "nail" and "nail surface" mean the natural, keratinaceous nail surface, or a natural nail to which an artificial nail or nail tip is adhered. In other words, the polymerizable compositions of the invention may be applied directly to the keratinaceous surface of the natural nail, or to a nail surface having affixed thereto an artificial nail or nail tip enhancement.

Nail Coatings

The present application describes nail coatings. As compared to conventional nail enamels, the nail coating of the present embodiments has a major advantage in that it enables the nail coating, which may also contain color, to adhere to the natural nail for long wear periods without adhesion loss or other signs of breakdown of the coating. The improved wear is achieved without the need of surface prepping the nail, such as with the use of primers or by slightly roughing the surface with a file or other means. For example, the nail coating of the present embodiments may be applied directly to the nail.

In some embodiments, it may be recommended to simply clean the surface of the nail to remove excess dirt and/or excess of natural oils. Cleaning of the nail surface may be achieved with the light use of solvent such as isopropyl alcohol or acetone.

According to one aspect, the invention is a single layer nail coating that may contain color and exhibits enhanced adhesion to the nail surface to resist chipping and peeling. According to an aspect, the disclosure provides a primer for pre-treating a nail surface before application of a nail coating that may, for example, improve adhesion of the nail coating to the nail surface, compared to an untreated nail. According to an aspect, the disclosure provides a nail coating that is a basecoat interposed between the nail surface and an additional layer that may enhance appearance, e.g. by providing a gloss finish or containing color or may provide a protective surface. According to an aspect, the disclosure provides a color layer that is applied to an exposed surface of a basecoat. According to an aspect, the disclosure provides a protective topcoat that is applied to an exposed surface of a color layer or basecoat.

Nail coatings of the invention achieve enhanced adhesion by the incorporation of a polyhedral oligomeric silsesquioxane, as defined further below, into the composition that is applied to the nail. Nail coatings of the invention provide enhanced adhesion to the nail surface, including natural nails and artificial nails, and, when used in multilayer systems, interlaminar adhesion between the various layers. As such, the nail coatings have longer wear characteristics, i.e. remain intact on the nail surface for longer periods of time. In most cases, the inventive nail coatings remain readily removable by use of suitable solvents.

A number of nail coating systems can demonstrate enhanced adhesion by the incorporation of a polyhedral oligomeric silsesquioxane. Among these are polymerizable nail coating systems; film-forming nail coating systems; water based nail coating systems; and liquid-and-powder nail coating systems. Each of these nail coating systems, and the components that may be used in nail coating formulations according to each system, is described in greater detail below.

Polyhedral Oligomeric Silsesquioxanes or "POSS"

Embodiments of the present invention incorporate Polyhedral Oligomeric (or Oligo) Silsesquioxane (POSS) into nail coatings. These compounds are distinguished from other silicone resins by their rigid three-dimensional cage-like structures. In some embodiments, the POSS used in the present embodiments has a three dimensional cage structure formed of a plurality of Si subunits, i.e. Si—O subunits, at least one of the subunits having one or more R groups. In some embodiments, the term "POSS" may refer to POSS molecules having 8 Si atoms or less (e.g., 6, 7 or 8), while EPOSS (extended Polyhedral Oligomeric (or Oligo) Silsesquioxane) may be used to refer to structures those cage structures having greater than 8 Si atoms. All silicone resins forming the cage structure may be used in the present embodiments. Accordingly, unless indicated otherwise, the term "POSS" refers to POSS or EPOSS molecules regardless of the number of Si atoms.

POSS are inorganic materials with a silica core and reactive functional groups on the surface and represented by the general formula of $RSiO_{1.5}$. Generally POSS are nano-sized, but may be larger depending upon the number of Si and O atoms in the structure, as well as substituents that might be present as described elsewhere herein. Cubic silsesquioxanes, such as octa(dimethylsiloxy) silsesquioxane ($R_8Si_8O_{12}$), consist of a rigid, crystalline silica-like core that is well-defined spatially (0.5-0.7 nm) which can be linked covalently to 8 R groups. A description of possible cages is discussed in U.S. Pat. No. 5,942,638, which is incorporated by reference in its entirety. Each of the cages can be further modified by attaching reactive moieties to the cage atoms. Depending upon the substituents, the core can account for approximately 5% of the total volume and the highly enhanced surface effects. The structure of the organic phase between the rigid, hard particles can be varied systematically; the potential exists to carefully tune mechanical, optical properties to establish structure-property relationships. For example, by varying the functionality of the R group it is possible to create multi-functionalized macromonomers, for example octa-functional macromonomers that will self-polymerize or copolymerize with other functionalized cubes to provide nanocomposites whose length scales and interfacial interactions are well-defined. Also by varying the functionality of the R group it is possible to enhance physical and chemical interactions between a nail surface and the coating or between coating layers in a multi-layer system to provide for the enhanced adhesion observed.

In some embodiments, POSS refers to only those compounds existing in a rigid, "cage"-type configuration, examples of which are shown in Formulas I-V, below. In some embodiments, POSS refers to only certain structures, such as, by way of non-limiting examples, those illustrated in Formulas I, III and IVA, which are referred to herein as being "complete cages" wherein all of the sides of the three-dimensional structure are completed sides and all of the Si atoms are completely saturated.

In some embodiments, the nail coatings of the present disclosure do not include other POSS that can exist, for example, in the ladder configuration of Formula VI and such as the polymethylsilsesquioxane known as Resin MK, has previously been disclosed in connection with cosmetic formulations in U.S. Pat. App. Pub. No. 2002/0114773, which is incorporated by reference in its entirety. As disclosed therein, the belief is that the compounds exist in both a "cage" (i.e., Formula I, wherein $R_1$-$R_8$ are $CH_3$—) and "ladder" configuration (Formula VI). It is also believed that the majority of the silicone polymers are present in the "ladder" configuration (Formula VI). To the extent that this composition contains the "ladder" configuration, it is not POSS as that term is used with respect to the present invention.

The POSS used in the nail coatings of the present embodiments may form the three-dimensional cage structure. In some embodiments, the POSS has at least 6 Si molecules. In some embodiments, the POSS contains 8 Si atoms. POSS may also include greater than 8 Si atoms or in mixtures containing, for example, 6-12 Si atoms or 8-12 Si atoms, for example as a mixture of compounds containing 8, 10 and 12 Si atoms. The number of Si atoms can also range from 6 to 100, alternatively 6 to 30, also alternatively 6 to 20 and finally alternatively 6 to 16, either as a single POSS structure (i.e. having the same configuration of Si and O atoms even if other substituents vary) or as a mixture of compounds with varying numbers of Si atoms with the same or varying R groups. In some embodiments, at least 4 of the Si atoms are bound, through an oxygen atom, to at least 3 other Si atoms (referred to herein as being "completely saturated"). All of the Si atoms are bound to at least one other Si atom through an oxygen bridge.

As shown in the exemplary and non-limiting structures of Formulas I through V and VII through X, POSS forms a rigid three-dimensional cage structure having at least two completed sides. This rigid cage structure is distinguished from ladders and other structures which are not held in place in three directions (see Formula VI for an exemplary ladder structure). Each of the Si atoms is bound to at least 1 R group with no more than 3, no more than 2 or no more than 1 Si atom being bound to more than 2 R groups. For example, the POSS molecule illustrated by Formula III has 6 saturated Si atoms and 5 complete sides (2 sides bounded by 3 Si atoms connected through oxygen bridges and 3 sides bounded by 4 Si atoms connected through oxygen bridges). Formula IIB has 4 such saturated Si atoms and 2 completed sides, both bounded by 4 Si atoms connected through oxygen bridges. Formula IIC has 6 saturated Si atoms and 3 completed sides all bounded by 4 Si atoms connected through oxygen bridges.

POSS molecules in accordance with some embodiments have the complete cage structure of Formula I:

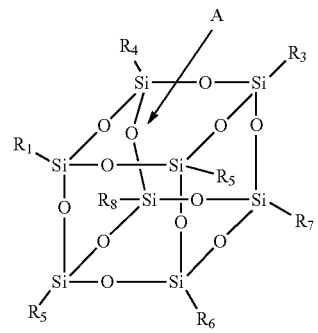

Formula I

It is also possible that one or even two of the oxygen bridges between successive Si atoms are broken or missing, in which case the "POSS" is referred to as having an "incomplete" cage structure. By way of non-limiting examples, consider the rigid three-dimensional cage structures illustrated in Formulas IIA-E:

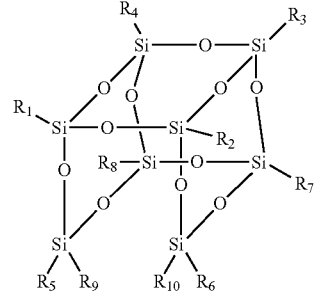

Formula IIA

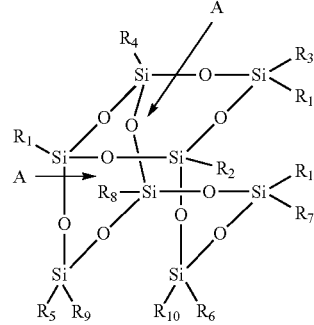

Formula IIB

Formula IIC
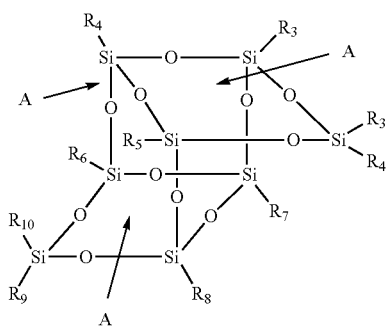
Formula IID
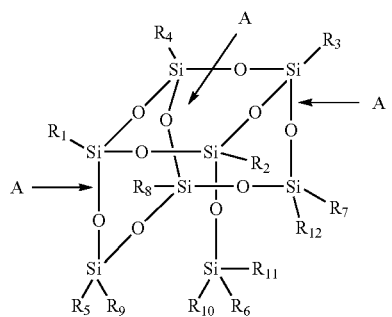
Formula IIE
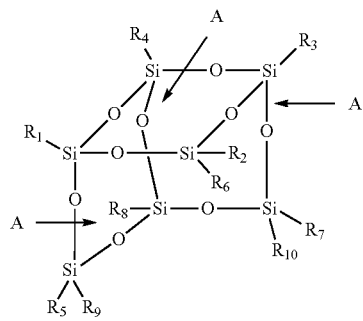
Formula III is a complete cage, but produced from 6 Si atoms.
Formula III
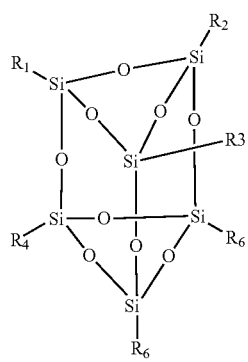
In Formula IVA, the number of Si atoms in the cage is 10, in Formula IVB, the number of Si atoms is 10 and in Formula IVC, the number of Si atoms in the cage is 12. In Formula IVD and IVE, the number of Si atoms in the cage or core is 16.
Formula IVA
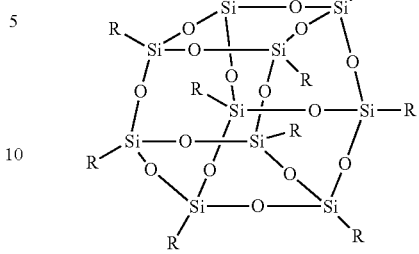
Formula IVB
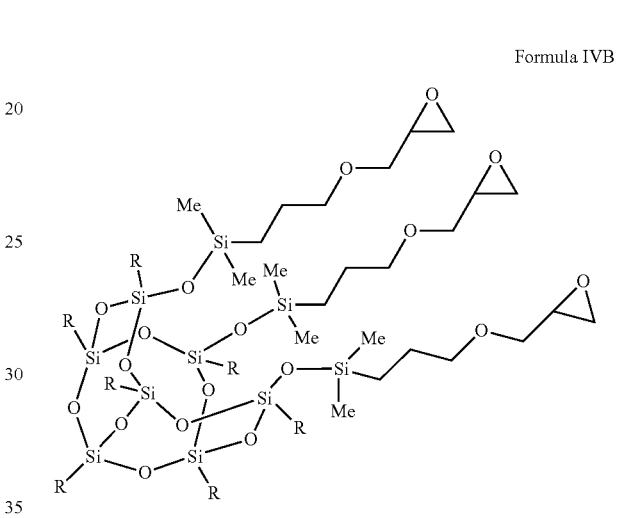
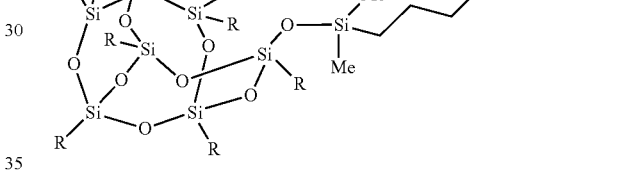
Formula IVC
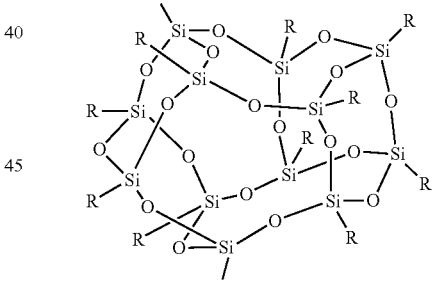
Formula IVD
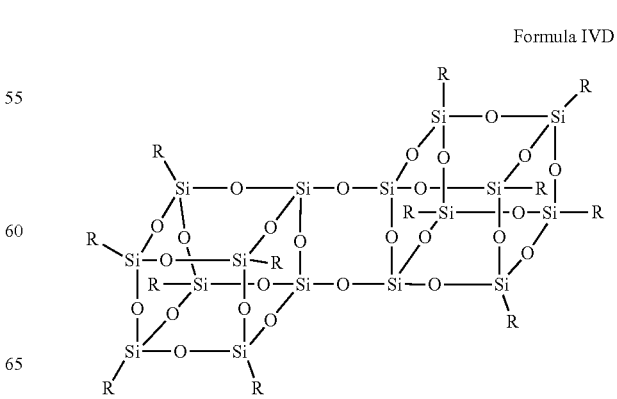

Formula IVE

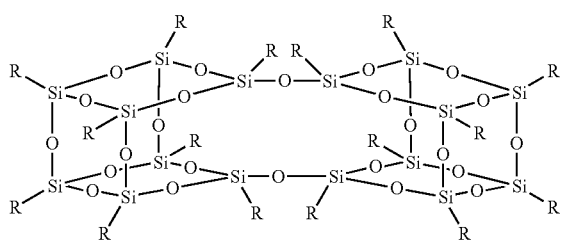

An example of an "incomplete" cage structure, wherein one or more of the oxygen bridges between successive Si atoms is broken or missing, is illustrated in Formula V:

Formula V

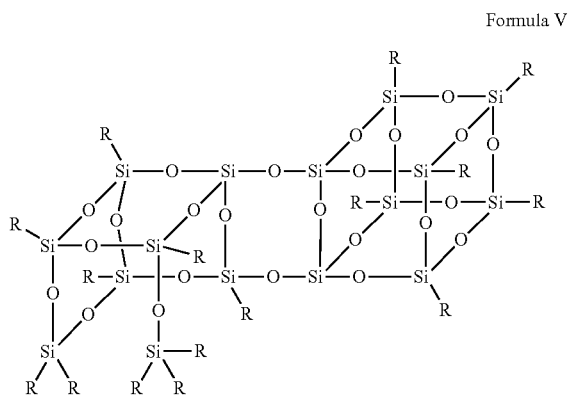

Formula VI, a ladder configuration (not a POSS according to the present embodiments/disclosure), can be a monomer linked end to end to other similar structures. It is not rigid within the meaning of this document as it can fold or flex around each R—Si—O—Si—R axis of the molecule. No such movement is possible in the rigid 3-D cage structures (whether complete or incomplete) of the POSS of the present embodiments. Thus, the molecules of this formula are not POSS.

Formula VI

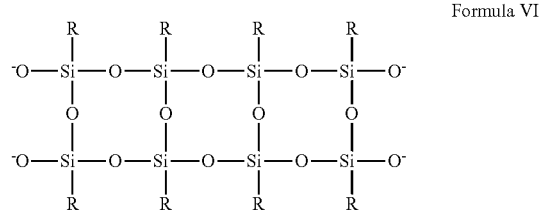

Note also that when referencing POSS molecules as being in accordance with Formula II, having the structure of Formula II, or being other than a completed cage, the sides which are illustrated as "open," "missing" or "broken" are illustrative only. When reference is made to Formula II, it is understood that any one or two sides, or any one or two oxygen bridges, may be broken or missing. The structure of the POSS molecule can be roughly thought of as a box (prism in the case of Formula III) or cage in shape with silicon (Si) atoms at each corner. Each Si atom is connected to at least one other Si atom through bonds to an oxygen atom (also referred to as an "oxygen bridge"). Preferably, at least 4 of the Si atoms in the POSS structure are "completely saturated." As used herein, a Si atom is "completely saturated" if bound, through oxygen atoms, to three other Si atoms within the cage as shown in Formulas I, III and IVA, most preferably, all of the Si atoms are "completely saturated". While illustrated in Formula I as Si atoms, the groups at each corner may be the same or different and may be one or more atoms or groups including, without limitation, silicon, silane, siloxane, silicone or organometallic groups. The POSS used in the invention can have a rigid 3-dimensional cage structure as illustrated, for example, in Formulas I-V and VII-X and the cage has at least two completed sides A. Each Si is bound to at least 1 R group. In some embodiments no more than 1 Si atom is bound to more than 2 R groups. In some embodiments no more than 2 Si atoms are bound to more than 2 R groups. In some embodiments no more than 3 Si atoms are bound to more than 2 R groups.

In some embodiments, POSS materials can be represented by the formula $[RSiO_{1.5}]\infty$ where $\infty$ represents molar degree of polymerization and R represents an organic substituent (H, siloxy, cyclic or linear aliphatic or aromatic groups that may additionally contain reactive functionalities such as alcohols, esters, amines, ketones, olefins, ethers or halides or which may contain fluorinated groups). The POSS used in the invention may be either homoleptic or heteroleptic. Homoleptic systems contain only one type of R group while heteroleptic systems contain more than one type of R group. In embodiments, the internal cage like framework is primarily comprised of inorganic silicon-oxygen bonds while the exterior of the nanostructure is covered by reactive and/or nonreactive organic functionalities (R), which ensure compatibility and tailorability of the nanostructure with organic monomers and polymers.

POSS compositions can be represented by the formulas:

$[(RSiO_{1.5})_n]_{\Sigma\#}$ for homoleptic compositions, $[(RSiO_{1.5})n(R'SiO_{1.5})_m]_{\Sigma\#}$ for heteroleptic compositions (where R≠ R'), $[(RSiO_{1.5})_n(XSiO_{1.5})_m]_{\Sigma\#}$ for functionalized heteroleptic compositions having a closed cage structure (where R groups can be equivalent or inequivalent). A functionalized heteroleptic POSS composition having an open cage structure may be represented by the formula $[(RSiO_{1.5})_n(RX-SiO_{1.0})_m]_{\Sigma\#}$.

By way of example, homoleptic POSS of Formulas III, I, IVA and IVC are designated as $[(RSiO_{1.5})_6]$, $[(RSiO_{1.5})_6]_{\Sigma 6}$, $[(RSiO_{1.5})_8]_{\Sigma 8}$, $[(RSiO_{1.5})_{10}]_{\Sigma 10}$ and $[(RSiO_{1.5})_{12}]_{\Sigma 12}$, respectively. Similarly, functionalized heteroleptic open cage POSS can have the following structures and designations:

Formula VII

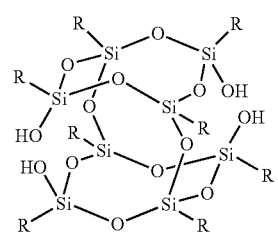

$[(RSiO_{1.5})_6(R(HO)SiO)_2]_{\Sigma 8}$

-continued

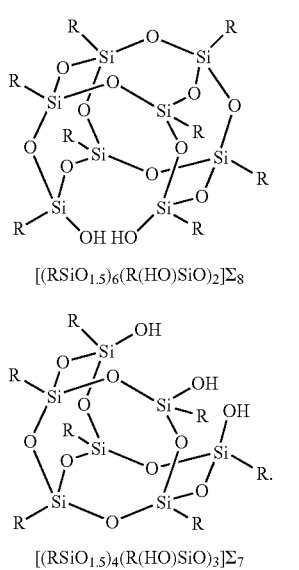

Formula VIII $[(RSiO_{1.5})_6(R(HO)SiO)_2]\Sigma_8$

Formula IX $[(RSiO_{1.5})_4(R(HO)SiO)_3]\Sigma_7$

In all of the above structures and formulas, R is the same or different and can be any of the moieties as defined elsewhere herein and X includes but is not limited to OH, Cl, Br, I, alkoxide (OR), acetate ($CH_3COOR$), acid (COOH), ester (COOR), peroxide (OOR), amine ($NR_2$), isocyanate (NCO), epoxy, olefin and R. The symbols m and n refer to the stoichiometry of the composition. The symbol $\Sigma$ indicates that the composition forms a nanostructure and the symbol # refers to the number of Si atoms contained within the nanostructure. The value for # is usually the sum of m+n, where n ranges typically from 1 to 24 and m ranges typically from 1 to 12. It should be noted that $\Sigma$# is not to be confused as a multiplier for determining stoichiometry, as it merely describes the overall nanostructural characteristics of the system (aka cage size).

Examples of attributes that enable nanostructured chemicals to function as 1-10 nm reinforcing and adhesion promoting agents include: (1) their unique size with respect to polymer chain dimensions, and (2) their ability to be compatibilized with polymer systems to overcome repulsive forces that promote incompatibility and expulsion of the nanoreinforcing agent by the polymer chains. That is, nanostructured chemicals can be tailored to exhibit preferential affinity/compatibility with a wide range of nail coating compositions through variation of the R groups on each nanostructure. Therefore, the factors to effect a selective nanoreinforcement include specific nanosizes of nanostructured chemicals, distributions of nanosizes, and compatibilities and disparities between the nanostrucutured chemical and the nail coating system.

The POSS used in the present invention is typically "derivatized" with one or more R groups that include a functional group. Other R groups may not include functional groups, but can be varied to modify the POSS by, for example, enhancing compatibility with solvents or other components of the nail coating, varying the size of the POSS to alter physical characteristics of the final coating, or enhancing solubility of the POSS in the nail coating. As non-limiting examples, one or more R groups could be an alkyl group, alkene, alkyne, hydroxyl, thiol, ester, acid, ether. In some embodiments, the "R groups" include, without limitation, one or more of the following: hydrogen, methyl, ethyl, propyl, isobutyl, isooctyl, phenyl, cyclohexyl, cyclopentyl, $-OSi(CH_3)_2-CH_2-CH_2-(CF_2)_5CF_3$, $-(CH_2)_3SH$, $N^+(CH_3)_3$, $O^-N^+(CH_3)_3$, $-OH$, $-(CH_2)_nN^+H_3X^-$ wherein n is 0-30 and X is a counter ion,

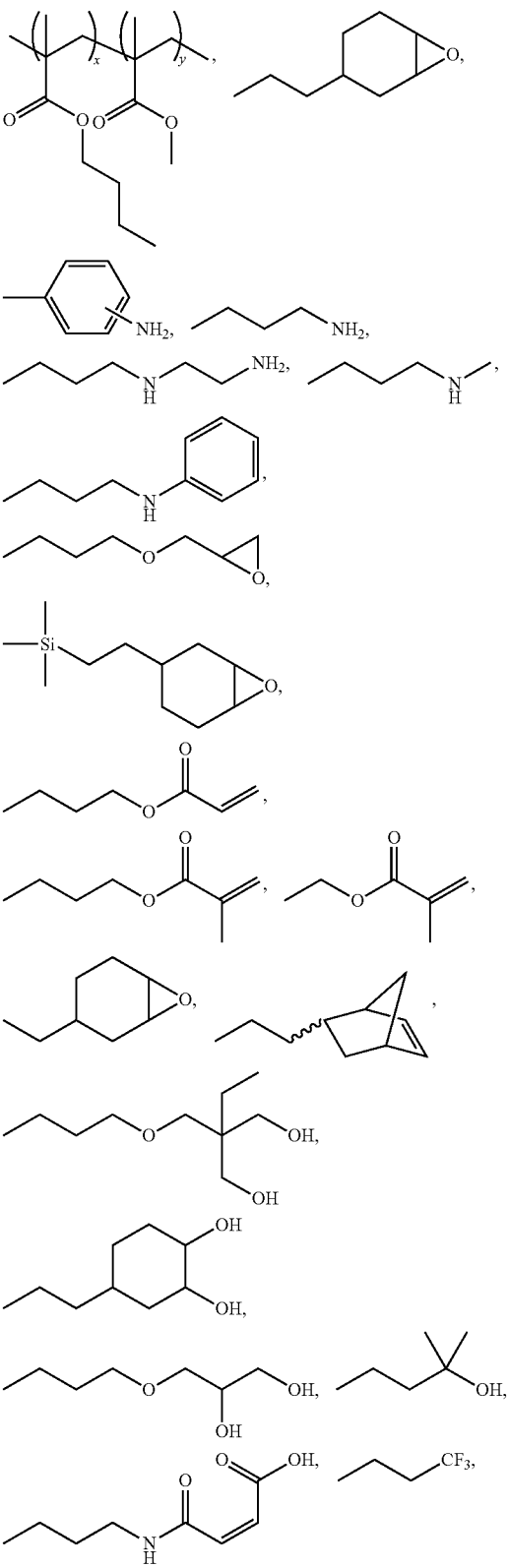

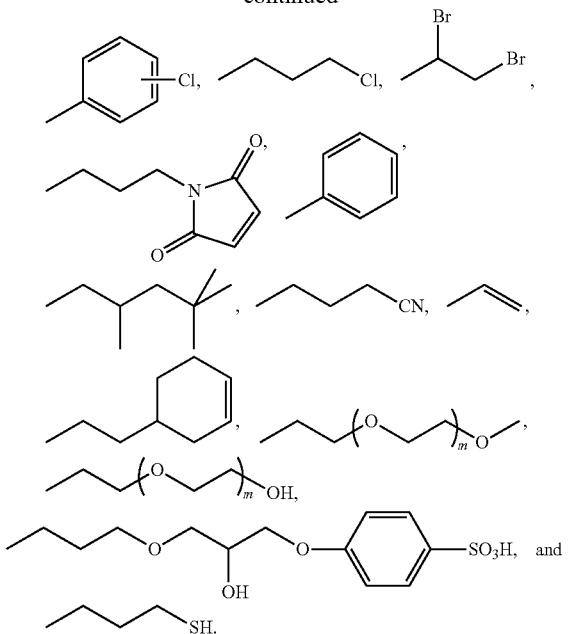

In some embodiments, R can also be a silane or siloxane structure, including a ladder structure. Formula X is a non-limiting example of a siloxane substituted POSS:

Formula X

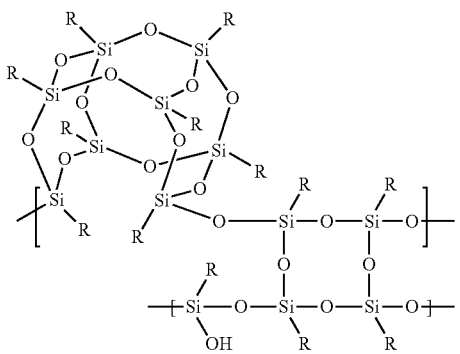

As previously illustrated (see Formulas IVD and IV E, the substituent can be an additional caged structure. In these instances, the structure can be considered conceptually as either a single POSS structure, as identified above, or as a POSS structure substituted by another POSS structure.

For example, the one remaining bond of each silicon of Formula I, III and IVA can bind to a variety of substituents or groups specified, as "R" groups ($R_1$-$R_8$), (($R_1$-$R_6$) in Formula III). As used herein, when multiple R groups are present on the same POSS molecule, each R group may be the same or different whether all are designated as simply R or differentiated as $R_1$, $R_2$, $R_3$, ... $R_n$. In some embodiments illustrated in Formulas II, IVB and V a POSS molecule in which one or two of the oxygen bridges between adjacent silicon molecules have been eliminated, a greater number of R groups are possible. When a POSS having 8 Si atoms is employed, it is preferred that no more than two of these inter-silicon connections (oxygen bridges) be eliminated. However, it is possible to eliminate as many as three such bridges (Formula IIE). More preferably, only a single oxygen bridge would be eliminated (Formula IIA). As stated above, the Si molecules not completely bound may have one or more additional positions available for binding additional substituents. In the case of a single missing side, the POSS molecule may include additional R groups $R_9$ and $R_{10}$, which may be the same or different as the $R_1$-$R_8$. When 2 or 3 bridges are missing, the POSS molecule may include additional R groups $R_9$, $R_{10}$, $R_{11}$ and $R_{12}$ (as appropriate), which all may be the same or different and may be the same as the groups identified for $R_1$-$R_8$.

POSS compounds with various R groups are known in the literature. They are described in a number of patents including, without limitation, U.S. Pat. Nos. 5,047,492, 5,389,726, 5,484,867, 5,589,562, 5,750,741, 5,858,544, 5,939,576, 5,942,638, 6,100,417, 6,127,557, 6,207,364, 6,252,030, 6,270,561, 6,277,451, 6,362,279 and 6,486,254. These patents describe in detail various methods of producing the basic POSS cage structure and various derivatives thereof, including POSS based polymers. To the extent that these patents identify and describe various POSS molecules having the structures of Formulas I-V and VII-X, derivatives and polymers thereof, they are incorporated by reference. The discussions of techniques for manufacturing and derivatizing this class of compounds described in each of these patents is also hereby incorporated by reference.

In general, R groups (for example, $R_1$, $R_2$, $R_3$, $R_4$, $R_5$, $R_6$, $R_7$, $R_8$, $R_9$, $R_{10}$, $R_{11}$ and $R_{12}$ as shown in the figures and any other R groups appropriate) can be the same or different and may be reactive or nonreactive groups. They may be, in replacing a methyl or H, for example, hydroxy (—OH), alkane derivatives (missing a hydrogen) also known as alkyl groups (other than methyl), alkenyl groups also referred to as derivatives of alkenes (having one or more double bonds), usually missing an H where they are bound to Si in POSS or to some other molecule, alkynyl groups also referred to as derivatives of alkynes (having one or more triple bonds) usually missing an H where they are bound to Si in POSS or to some other molecule, aryl groups (either the 6-carbon ring of benzene or the condensed 6-carbon rings of other aromatic derivatives such as naphthalene) also referred to as derivatives of arenes, usually missing an H where they are bound to Si in POSS or to some other molecule, heteroaryl groups (either a 6-membered or 5-membered aromatic ring containing one or more atoms other than carbon in the ring, e.g. N, S or O, or structures containing condensed heteroaromatic rings) acyl groups (organic acids without the OH group, e.g., $CH_3CO$— or $C_6H_5CO$—), alkoxy groups (alkyl radicals attached to the remainder of a molecule by oxygen), such as methoxy, ester groups, acid groups, acrylate groups, alkyl acrylate groups, hydroxy groups, halogens, amino groups, alkylamino groups, aminoalkyl groups, groups containing one or more tertiary or quaternary nitrogens, silicone containing groups, sulfur containing groups, epoxides, azo groups, diazo groups, halogens, cyclic compounds which can undergo ring opening polymerization or ring opening metathesis polymerization. R groups may also be monomers or polymers where POSS will be used as a pendant substituent of the polymer. Acrylates and cationic polymers providing conditioning properties are provided in some embodiments.

Where appropriate, any of these R groups may themselves be substituted or unsubstituted, saturated or unsaturated, linear or branched. Possible substitutions include $C_1$-$C_{30}$ alkyl groups, $C_1$-$C_{30}$ alkenyl groups, $C_1$-$C_{30}$ alkynyl groups, $C_6$-$C_{18}$ aryl groups, acyl groups, alkoxy or other groups, carboxy groups, ester groups, acrylate groups, alkyl acrylate groups, trihydroxy groups, amino groups, alkylamino groups including mono and dialkylamino groups, mono and dihydroxy alkylamino groups, cyano groups, aminoalkyl groups, groups containing one or more tertiary or quaternary nitrogens, silicone containing groups, sulfur and/or phosphorous containing groups, $SO_2X$, $SO_3X$, where X is H, methyl or ethyl, epoxides and epoxide containing groups, azo groups, diazo groups, halogens, cyclic compounds which can undergo ring opening polymerization or ring opening metathesis polymerization. Indeed, any group which can be attached to a corner of a POSS molecule can be used.

When these R groups are carbon containing fatty acids or fatty alcohols, aromatic or cyclic groups, they generally may contain between 6 and 50 carbon atoms and may be saturated or unsaturated, substituted as discussed above or unsubstituted and branched or linear, as appropriate for a given group.

More specifically, possible R groups include, without limitation, hydroxy groups including mono or poly hydroxy groups, phenols, alkoxy, hydroxy alkyls, silanes, amino and in particular, quats, halosilanes, epoxides, alkyl carbonyls, alkanes, haloalkyls, halogens, acrylates, methacrylates, thiols, nitriles, norbornenyls, branched alkyl groups, polymers, silanes, silanols, styryls and thiols. In a single POSS molecule of Formula I, $R_1$ could be H, $R_2$—OH, $R_3$—$NH_2$, $R_4$—$CH_2CH_2N^+CH_3(OCH_2CH_3)CH_2CH_2CH_3$, $R_5$—$CH_2CH_2CHOCH_2$ (epoxide), $R_6$—$OC(CH_3)_3$, $R_7$—$OOC(CH_2)_{16}CH_3$ and $R_8$ could be Cl. This is a hypothetical example, merely to illustrate that each of the R groups can be derivatized separately and to emphasize the wide variety of possible substitutions.

In some embodiments, these POSS molecules are not completely substituted with the same R groups (e.g., not all $R_1$-$R_6$, $R_1$-$R_8$, $R_1$-$R_{10}$ or $R_1$-$R_{12}$ (and any other R groups, as appropriate, given the number of Si atoms and available bonds in a given POSS molecule) are methyl, isobutyl or phenyl). This is particularly preferred for POSS molecules that have the structure of Formula I. Moreover, when a POSS molecule having 8 Si subunits, as depicted in Formula I, is employed, at least one of the R groups is a group other than a methyl, particularly where the silicon resin is a T resin and, even more particularly, Resin MK.

Also contemplated under the term POSS is the family of commercially available compounds available from Hybrid Plastics, 55 W. L. Runnels Industrial Drive Hattiesburg, MS 39401 and Mayaterials, Inc. P.O. Box 87, South Lyon, Mich. 48178-0087.

In some embodiments, the POSS used in the coatings (nail coating or nail topcoat) of the present embodiments has the formula of $(C_6H_{11}O_2)_n(SiO_{1.5})_n$, where n is 6 (see Formula III), 8 (see Formula I), 10 (see Formula IVA), or 12 (see Formula IVC) and $C_6H_{11}O_2$ represents a glycidyl epoxide having the structure:

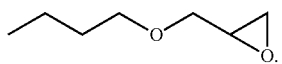

In some embodiments, the POSS used in the coatings of the present embodiments has the formula of $(C_6H_{11}O_2)_n(SiO_{1.5})_n$, where n is 8, 10, or 12. In some embodiments, the POSS used in the coatings of the present embodiments has formula of $(C_6H_{11}O_2)_n(SiO_{1.5})_n$, where n is 8 or 10. In some embodiments, the POSS used in the coatings of the present embodiments has the formula of $(C_6H_{11}O_2)_n(SiO_{1.5})_n$, where n is 8. In some embodiments, the POSS used in the coatings of the present embodiments is a mixture of POSS structures having the formula $(C_6H_{11}O_2)_n(SiO_{1.5})_n$, where n is 6, 8, 10, and 12. In some embodiments, the POSS used in the coatings of the present embodiments is a mixture of POSS structures having the formula $(C_6H_{11}O_2)_n(SiO_{1.5})_n$, where n is 8, 10 and 12. In some embodiments, the POSS used in the coatings of the present embodiments is a mixture of POSS structures having the formula of $(C_6H_{11}O_2)_n(SiO_{1.5})_n$, where n is 8 and 10.

In some embodiments, the POSS molecules are functionalized with at least one group or a plurality of groups. Examples of functional groups on the polymer and POSS materials include, but are not limited to, functional silicones—for example, hydroxy, urethane, acrylate, vinyl, Si—H, amides, functional acrylates, functional polyamides, Poly(9-vinylcarbazole) (PVK), Polyvinyl Acetate (PVA), Polystyrene (PS), Polyethylene Glycol (PEG), Polypropylene Glycol (PPG), polysaccharides or modified starch, functional block copolymers, functional polyesters and polyethers, fluorinated polymers and wax to bring about the cross-linking reaction between the polymer chains and POSS materials to provide desired properties.

The POSS of the present invention may be prepared by hydrolytic condensation reactions of trifunctional organosilicone monomers, e.g. RSi(OMe). Methods of preparing POSS are described in U.S. Pat. Nos. 8,133,478 and 6,372,843, which are incorporated herein by reference in their entireties.

In some embodiments, the POSS used in the coatings of the present embodiments is Glycidyl POSS® Cage Mixture (sold by Hybrid Plastics as EP0409), which is a blend of caged and non-caged structures as described in, for example, U.S. Pat. Nos. 6,716,919 and 6,927,270, each of which is incorporated herein by reference in its entirety. In some embodiments, the POSS used in the coatings of the present embodiments is Acrylo POSS® Cage Mixture (sold by Hybrid Plastics as MA0736), Epoxycyclohexyl POSS® Cage Mixture (sold by Hybrid Plastics as EP0408), NorbornenylethylDiSilanol-isobutyl POSS® (sold by Hybrid Plastics as NB 1038), TMP Diol-isobutyl POSS® (sold by Hybrid Plastics as AL0104), Trans-Cyclohexanediol-isobutyl POSS® (sold by Hybrid Plastics as AL0125), 1,2-Propanediol-isobutyl POSS® (sold by Hybrid Plastics as AL0130), Octa(3-hydroxy-3-methylbutyldimethylsiloxy) POSS® AL01361, Amic Acid-Cyclohexyl POSS® (sold by Hybrid Plastics as CA0295), Maleamic Acid-Isobutyl POSS® (sold by Hybrid Plastics as CA0296), OctaMaleamic Acid POSS® (sold by Hybrid Plastics as CA0298), Epoxycyclohexylisobutyl POSS® (sold by Hybrid Plastics as EP0402), Glycidylehtyl POSS® (sold by Hybrid Plastics as EP0417), Glycidylisobutyl POSS® (sold by Hybrid Plastics as EP0418), GlycidylPhenyl POSS® (sold by Hybrid Plastics as EP0419), Tryblycidyl Cyclohexyl POSS® (sold by Hybrid Plastics as EP0421), Tryglycidylisobutyl POSS® (sold by Hybrid Plastics as EP0423), Octa Epoxycyclohexyl dimethylsilyl POSS® (sold by Hybrid Plastics as EP0430), OctaGlycidyldimethylsilyl POSS® (sold by Hybrid Plastics as EP0435), Trifluoropropyl POSS® Cage Mixture (sold by Hybrid Plastics as FL0578), Trifluoropropylisobutyl POSS® (sold by Hybrid Plastics as FL0583), Chlorobenzylethylisobutyl POSS® (sold by Hybrid Plastics as HA0605), Aminoethylaminopropylisobutyl POSS® (sold by Hybrid Plastics as HA0615), Chloropropvlisobutyl POSS® (sold by Hybrid Plastics as HA0635), Octakis(dibromoethyl) POSS® (sold by Hybrid Plastics as HA0640), Maleimide Cyclohexyl POSS® (sold by Hybrid Plastics as IM0670), POSS® Maleimide Isobutyl (sold by Hybrid Plastics as IM0673), Acryloisobutyl (sold by Hybrid Plastics as MA0701), Methacryloisobutyl POSS® (sold by Hybrid Plastics as MA0702), Methacrylate Cyclohexyl POSS® (sold by Hybrid Plastics as MA0703), Methacrylate Isobutyl POSS® (sold by Hybrid Plastics as MA0706), Methacrylate Ethyl POSS® (sold by Hybrid Plastics as MA0716), Methacryl-Ethyl POSS® (sold by Hybrid Plastics as MA0717), Methacrylate Isooctyl POSS® (sold by Hybrid Plastics as MA0718), Methacrylisooctyl POSS® (sold by Hybrid Plastics as MA0719), MethacrylPhenyl POSS® (sold by Hybrid Plastics as MA0734), Methacryl POSS® Cage Mixture (sold by Hybrid Plastics as MA0735), Acrylo POSS® Cage Mixture (sold by Hybrid Plastics as MA0736), DodecaPhenyl POSS® (sold by Hybrid Plastics as MS0802), Isooctyl POSS® Cage Mixture (sold by Hybrid Plastics as MS0805), Phenylisobutyl POSS® (sold by Hybrid Plastics as MS0813), Phenylisooctyl POSS® (sold by Hybrid Plastics as MS0814), IsooctylPhenyl POSS® (sold by Hybrid Plastics as MS0815), Octaisobutyl POSS® (sold by Hybrid Plastics as MS0825), OctaMethyl POSS® (sold by Hybrid Plastics as MS0830), OctaPhenyl POSS® (sold by Hybrid Plastics as MS0840), Octatetramethyl ammonium POSS® (sold by Hybrid Plastics as MS0860), OctaTrimethylsiloxy POSS® (sold by Hybrid Plastics as MS0865), Cyanopropylisobutyl POSS® (sold by Hybrid Plastics as NI0914), (sold by Hybrid Plastics as NB1000), 1,3-Bis(Norbornenylethyl)-1,1,3,3-tetramethyldisiloxane (sold by Hybrid Plastics as NB1010, Norbornenylethyldimethylchlorosilane (sold by Hybrid Plastics as NB10171 Norbomenylethylethyl POSS® (sold by Hybrid Plastics as NB 1021), Norbornenylethylisobutyl POSS® (sold by Hybrid Plastics as NB 1022), NorbornenylethylDiSilanol-isobutyl POSS® (sold by Hybrid Plastics as NB 1038), Trisnorbornenyl-isobutyl POSS® (sold by Hybrid Plastics as NB1070), Allysobutyl POSS® (sold by Hybrid Plastics as OL11181 Vinyl-isobutyl POSS® (sold by Hybrid Plastics as OL1123), Octacyclohexenyldimethylsilyl POSS® (sold by Hybrid Plastics as OL1159), Octavinylsilsesquioxane POSS® (sold by Hybrid Plastics as OL1160), OctaVinyldimethylsilyl POSS® (sold by Hybrid Plastics as OL1163), Vinyl POSS® Cage Mixture (sold by Hybrid Plastics as OL1170), PEG POSS® Cage Mixture (sold by Hybrid Plastics as PG1190), OctaSilane POSS® (sold by Hybrid Plastics as SH1310), Octahydrido POSS® (sold by Hybrid Plastics as SH1311), TriSilanolCyclohexyl POSS® (sold by Hybrid Plastics as SO1400), TriSilanolEthyl POSS® (sold by Hybrid Plastics as SO1444), TriSilanolisobutyl POSS® (sold by Hybrid Plastics as SO1450, TriSilanolisooctyl POSS® (sold by Hybrid Plastics as SO1455), TriSilanolPhenyl POSS® (sold by Hybrid Plastics as SO1457), TrisilanolPhenyl POSS® (sold by Hybrid Plastics as SO1458), TetraSilanolPhenyl POSS® (sold by Hybrid Plastics as SO1460), Tris sulfonic acid ethyl POSS® (sold by Hybrid Plastics as SA1532), Tris Sulfonic Acid Isobutyl POSS® (sold by Hybrid Plastics as SA1533), Mercaptopropylisobutyl POSS® (sold by Hybrid Plastics as TH1550), Mercaptopropyl i-octyl POSS® (sold by Hybrid Plastics as TH1555), OctaAmmonium POSS® (sold by Hybrid Plastics as AM0285), Aminopropylphenyl POSS® (sold by Hybrid Plastics as AM0273), Vinyl Silsesquioxane Resin (sold by Hybrid Plastics as PM1285MV), Octaaminophenyl POSS® (sold by Hybrid Plastics as AM0280), N-Phenylaminopropyl POSS® Cage Mixture (sold by Hybrid Plastics as AM0281), N-Methylaminopropylisobutyl POSS® (sold by Hybrid Plastics as AM0282), p-Aminophenyl Cyclohexyl POSS® (sold by Hybrid Plastics as AM02901, m-Aminophenyl Cyclohexyl POSS® (sold by Hybrid Plastics as AM0291), p-Aminophenylisobutyl POSS® (sold by Hybrid Plastics as AM0292), m-Aminophenylisobutyl POSS® (sold by Hybrid Plastics as AM02931 Aminoethylaminopropylisobutyl POSS® (sold by Hybrid Plastics as AM0275), Aminopropylisobutyl POSS® (sold by Hybrid Plastics as AM0265), PEG POSS® Cage Mixture (sold by Hybrid Plastics as PG1190), Aminopropylisooctyl POSS® (sold by Hybrid Plastics as AM0270), or a mixture thereof.

POSS Functionalized Monomers

POSS Functionalized Monomers possess a hybrid inorganic-organic three-dimensional structure which contains one or more reactive organic functional groups. Although referred to herein as "monomers", it is to be understood that the term reactive organic functional groups include groups that can polymerizable groups or groups that can otherwise interact with additional nail coating components or other POSS molecules to enhance physical properties of the nail coating such as adhesion and toughness. POSS Functionalized Monomers may contain non-reactive organic groups with one functionalized reactive group, multiple non-reactive organic groups and multiple functionalized reactive groups, or only functionalized reactive groups. For example, a POSS having eight R groups may contain seven non-reactive organic groups with one functionalized reactive group, six non-reactive organic groups and two functionalized reactive groups, five non-reactive organic groups and three functionalized reactive groups, etc. up to a POSS containing eight functionalized reactive groups. The unique functional groups can include, but are not limited to, amines, esters, epoxides, methacrylates, olefins, silanes, styryls, and thiols. By varying the functional group(s) and non-reactive organic group(s), a multitude of POSS Functionalized Monomers can be prepared. While the monofunctional POSS Monomers can be incorporated by copolymerization or grafting, multifunctional POSS Monomers, i.e. POSS containing more than one functionalized reactive group, can be utilized as effective cross-linkers. POSS Functionalized Monomers react similarly in polymerization, grafting and cross-linking reactions to standard organic monomers. While they react like simple organic monomers, when incorporated into a polymeric material, POSS Functionalized Monomers impart significant improvements in the thermal, mechanical, and gas separation properties of traditional plastics.

POSS Polymers and Resins

POSS Polymers and Resins possess a hybrid inorganic-organic composition and can be either thermoplastic or thermoset materials. As a class of materials, POSS Polymers and Resins are comprised of either (1) polymers in which a POSS Functionalized Monomer has been co-polymerized or grafted onto a polymer chain, or (2) silsesquioxane resins possessing some cage structure (see, e.g. Formula X). POSS Polymers and Resins can be used as stand-alone replacements for traditional materials or they may be compounded or solution blended into traditional polymeric materials to enhance the properties of the base resin. The types of POSS Polymers and Resins that are currently available include, but are not limited to, silicones, styrenics, acrylics, and norbornenes.

POSS molecules are available from Hybrid Plastics and include, without limitation, those based on Formulas I-IV. Other POSS products may be purchased from ALDRICH. Still others are described in U.S. Pat. Nos. 8,133,478, 5,047,492, 5,858,544 and 2,465,188, each of which is hereby incorporated by reference in its entirety.

Particularly preferred POSS molecules useful for producing coating compositions in accordance with the present embodiments include: TrisFluoro(13)Cyclopentyl-POSS® (FL0590); Mercaptopropyllsobutyl-POSS® (sold by Hybrid Plastics as TH1550); Mercaptopropyllsooctyl-POSS® (sold by Hybrid Plastics as TH1555); Poly(methacrylpropylisooctylPOSS®-co-methymethacrylate) 60% wt (sold by Hybrid Plastics as PM1275.4-60); Poly(Methacrylpropylisooctyl-POSS®-co-methylmethacrylate) 80% wt (sold by Hybrid Plastics as PM 1275.4-80); Octalsobutyl-POSS® (sold by Hybrid Plastics as MS0825); OctaPhenyl-POSS® (sold by Hybrid Plastics as MS0840); Isooctyl-POSS® Cage Mixture, 95% (sold by Hybrid Plastics as MS0805); EpoxyCyclohexylCyclohexyl-POSS® (sold by Hybrid Plastics as EP0399); EpoxyCyclohexyllsobutyl-POSS® (sold by Hybrid Plastics as EP0402); Glycidyl POSS® Cage Mixture (sold by Hybrid Plastics as EP0409); GlycidylCyclohexyl-POSS® (sold by Hybrid Plastics as EP0415); GlycidylIsobutyl-POSS® (sold by Hybrid Plastics as EP0418); TrisGlycidylCyclohexyl-POSS® (sold by Hybrid Plastics as EP0421); and OctaEpoxyCyclohexyldimethylsilyl-POSS® (sold by Hybrid Plastics as EP0430); OctaAminophenyl-POSS® (sold by Hybrid Plastics as AM0280); OctaAminophenyl-POSS® (sold by Hybrid Plastics as AM0285); Trimethoxy-[2-(7-oxabicyclo[4.1.0]hept-3-yl)ethyl]silane, hydrolyzed (sold by Hybrid Plastics as EP0408); Hydrolyzed [3-(Trimethoxysilyl)propyl]aniline (sold by Hybrid Plastics as AM0281); [(dimethyl(norbornenylethyl)silyloxy) dihydroxy]-POSS® (sold by Hybrid Plastics as NB1038); vinyl silsesquioxane resin-liquid (PM1285MV); Acrylo POSS® Cage Mixture (sold by Hybrid Plastics as MA0736); and OctaTMA-POSS® (sold by Hybrid Plastics as MS0860).

As illustrated in the non-limiting examples set forth below, a variety of POSS structures can be used in nail coating compositions. In some cases, an existing nail coating composition can be enhanced (e.g., by demonstrating enhanced adhesion) by addition of a POSS to the composition. The POSS can be selected to provide a desirable set of physical properties for the system being modified and that exhibits compatibility with the particular nail coating system. In a solvent based system, it is desirable that the POSS be present in a form that is soluble in the relevant solvent. For example, in an aqueous system, it is desirable that the POSS be present in a form that is water soluble. The POSS should also be selected such that it does not react undesirably with other components of the nail coating system during storage and prior to use. Consideration should also be given as to whether the POSS should react with other components of the system, for example by co-polymerization or other chemical reaction, or whether the POSS should interact primarily with either the nail surface, if applied as a single layer or a basecoat, or with another layer to promote interlaminar adhesion. The most desirable POSS for a particular application can be identified or selected based upon the desired properties and the substituents. Using routine experimentation, the organic groups (which can impart the desired properties such as solubility and reactivity) on the POSS can be varied or different FOSS molecules tested to arrive at the optimal POSS for a particular system.

According to the present invention, nail coatings can be obtained by either adding an appropriate POSS component to an existing nail coating system or by formulating an entirely new system. The nail coating system may be, for example, a single layer system, such as an enamel containing only a film forming component, a single layer photocurable system that includes polymerizable monomers such as a gel or acrylic, a solvent based system that includes both a film-forming component and a polymerizable component, or a water based nail coating. The POSS may be added in an amount of from about 0.01 wt % to about 20 wt % of the total composition before it is applied. For example, the POSS may be present in an amount of from about 0.05 wt % to about 10 wt %; from about 0.05 wt % to about 8 wt %; from about 0.05 wt % to about 5 wt %; from about 1 wt % to about 10 wt %; from about 1 wt % to about 8 wt %; from about 1 wt % to about 5 wt %; from about 2 wt % to about 10 wt %; from about 2 wt % to about 8 wt %; or from about 2 wt % to about 5 wt %. The POSS may be added in an amount of no greater than 20 wt %, no greater than 15 wt %, no greater than 10 wt %, no greater than 8 wt %, no greater than 5 wt %, no greater than 2 wt %, no greater than 1 wt %, or less.

The POSS may be added to an existing formulation directly; as a mixture with some other component of the system such as a solvent, film former such as a cellulosic polymer (e.g., a cellulose alkylate ester such as cellulose acetate butyrate or CAB), or a mixture of solvent and other components. Alternatively, the POSS may be incorporated during normal mixing and processing of used to prepare the nail coating composition.

Nail Coatings

The invention comprises the addition of POSS to a wide range of nail coatings and nail coating systems including nail enamels, polymerizable nail coatings (artificial nails, gels acrylics), hybrid systems, and nail primers. As stated above, the POSS can be added to an existing stock or base system or formulated as a part of the stock or base system. As used herein, "base system" refers to an existing nail coating that does not include POSS and is distinguished from a "basecoat" which refers to a nail coating applied directly to a nail prior to an additional coating. The various coating systems to which POSS can be added to enhance adhesive properties is described below, followed by a description of the various components that can be present in nail coating of the invention.

Nail coatings to which POSS can be added include those disclosed in, for example, U.S. Pat. Nos. 8,124,058, 6,818, 207, 8,399,537, 8,263,677, 8,367,742, 5,985,951, 5,785,958, 5,576,509, 5,965,147, 5,639,447, 6,051,242, 5,130,125, 5,512,273, 5,662,891, 5,720,804, 4,871,534, 5,785,958 and 7,678,321; in US Patent Application Publication Nos. 2010/0012263, 2005/0065297 and 2007/0286827; in PCT Application Publication Nos. WO 2011/011304, WO 2011/031578, WO 2011/043880 and WO 2011/043879; and in U.S. application Ser. Nos. 13/846,024 filed 18 Mar. 2013, Ser. No. 12/573,633 filed 5 Oct. 2009, Ser. No. 12/573,640 filed 5 Oct. 2009, Ser. No. 13/042,436 filed 7 Mar. 2011, Ser. No. 13/827,483 filed 14 Mar. 2013 and 61/692,096 filed 22 Aug. 2012. The disclosures of each of these patents, publications, and patent applications are hereby incorporated by reference in their entirety.

Types of Nail Coatings

Nail Enamels

Embodiments of the invention comprise a nail enamel composition for application to the nails which deposit a film on the nail after solvent evaporation. Nail enamel compositions are generally polymer based liquids with a film-forming polymer dissolved in an organic solvent such as an butyl acetate, ethyl acetate, isopropanol and the like, as well as mixtures thereof. After application to the nail, the solvent evaporates depositing the film forming composition and any pigments therein on the surface of the nail.

Polymerizable Nail Coatings (Gels, Acrylics and Hybrids)

Embodiments of the invention comprise a polymerizable composition for application to the nails and polymerization to yield a nail coating or an artificial nail structure. The polymerizable composition is preferably an anhydrous liquid, having the consistency of a semi-mobile gel to freely mobile liquid at room temperature. Immediately prior to use, the polymerizable composition is applied to the nail surface and shaped by the nail technician. After polymerization an artificial nail structure is obtained.

Multilayer

According to an aspect, the inventive coating is applied as three distinct layers, one or more of which may be at least partially cured. POSS can be present in any one or more layers of the coating. According to an aspect, application of any one of the layers may be omitted. According to an aspect, application of any two of the layers may be omitted. As such, it is contemplated that the coating can be applied as a one-layer, two-layer, or three-layer system. According to an aspect, only a formulation for a color layer comprises colorant agents. According to an aspect, a formulation for any of the layers may comprise colorant.

Aspects of the present disclosure provide a basecoat as a layer intermediate between the nail and coating surfaces. The inventive basecoat can be a polymerizable liquid, and provides a conformal coating over the nail surface. The basecoat may also contain a pigment or color. The inventive composition may be polymerizable with actinic radiation. The actinic radiation may be ultraviolet (UV) radiation. In some embodiments, no additional layers are applied over the basecoat.

Aspects of the present disclosure provide an intermediate layer that can be a decorative layer, for example a color layer. The intermediate layer may be applied to an exposed surface of a basecoat layer.

Aspects of the present disclosure provide a topcoat layer to be applied to an exposed surface of the basecoat or intermediate layer.

The one or more layers of a nail coating can include one or more components selected from the following categories of components: reactive monomers, and/or oligomers, and/or polymers; a high-molecular weight (meth)acrylate polymer or copolymer; a polymer which conveys enhanced adhesiveness and which confers solvent sensitivity to the polymerized lattice; a urethane methacrylate resin; a (meth) acrylate monomer which provides improved adhesion, viscosity, wear and durability; an aromatic or aliphatic (meth) acrylate monomer which may be present to improve adhesion; a monomer and/or oligomer providing one or more free hydroxyl groups; an adhesion promoter; a non-reactive, solvent-dissolvable polymer; an optional resin; a plasticizer; a UV stabilizing agent; a polymerization initiator/photoinitiator; a polymerization regulator; a color agent; and a solvent. These categories are described in greater detail below, and exemplary compounds from each category are discussed.

Water-Based Enamels

A water-based enamel nail coating formulation includes water as a solvent and a film-forming polymer. The water-based enamel nail coating formulation can include one or more of the following categories of components: a water-miscible (meth)acrylic acid polymer; a (meth)acrylate copolymer; a styrene-(meth)acrylate copolymer; a polyurethane film former and/or thickeners; an oligo- or polyoxyalkylene (e.g., a glycol ether, dipropylene glycol, n-butyl ether dipropylene glycol, a PEG or PPG, or diethylene glycol); a non-ionic soap; and a color agent. A water-based enamel is free of organic solvents such as ethyl acetate, butyl acetate, acetone, or the like. In some embodiments, a water-based enamel nail coating includes water, styrene acrylates copolymer (e.g., a styrene-(meth)acrylate copolymer), and acrylates copolymer (e.g., a (meth)acrylate copolymer).

Liquid-and-Powder Formulations

In some embodiments, a polymerizable nail coating is derived from the liquid-and-powder method. Immediately prior to use, an appropriate amount of a polymerizable nail coating composition comprised primarily of one or more liquid monomers is poured into a dish or other appropriate vessel. A brush or other shaping tool is dipped into the composition to form a small bead on the tip of the tool. This bead is then dipped into a polymer powder mixture, which is in a separate dish. Upon dipping the bead of liquid monomer on the brush into the polymer powder material, a doughy, adherent, agglomerated mass of particles is formed at the tip of the shaping tool. Alternatively, the powder can be slurried in the liquid to obtain a doughy mass, and the shaping tool is dipped into the doughy mass. Generally a ratio of 0.2 to 1.3 parts of polymer powder to 1 part of the liquid monomer composition will provide suitable polymerization. The liquid polymerizable nail coating composition softens and partially dissolves the powder. The tip of the shaping tool, with its load of doughy material is then used to sculpt a new nail shape on the nail surface. A polymerization initiator (e.g., a peroxide) in the powder and a polymerization accelerator (e.g., an amine) in the liquid monomer act together to catalyze polymerization of the monomer composition to result in an artificial nail structure, which is then shaped and polished as desired. In order for the polymerizable composition to exhibit a desirable workability, the composition should be such that when a 1 to 0.5, respectively, mixture of the polymerizable composition and the above mentioned powdered catalyst are mixed and stored at 15° C., the mixture should gel to a viscosity of 100,000 centipoise in 400 to 1400 seconds, preferably 600 to 1200 seconds, most preferably 800 to 1000 seconds. Liquid-and-powder compositions and methods are described in, for example, U.S. Pat. No. 6,818,207, which is incorporated by reference in its entirety.

The liquid monomer composition can include one or more ethylenically unsaturated monomers, such as one or more (meth)acrylate monomers. It can also optionally include a multicarbonyl-vinyl containing monomer; a plasticizer; a polymerization accelerator; a UV absorber; a polymerization regulator. Such liquid monomer compositions are described in U.S. Pat. No. 6,818,207, which is incorporated by reference in its entirety.

Suitable polymer powders are preferably polymers or copolymers which contain at least some ethylenic unsaturation to permit cross-linking. The polymer powder mixture is generally comprised of a linear particulate chain-extended or cross-linked acrylate or methacrylate polymer, which may be in the random or block copolymer form. Most typically the acrylate or methacrylate polymer is ethyl- or methyl methacrylate or ethyl- or methyl acrylate, or a combination of one or more of these polymers. Most often a copolymer of ethyl- and methyl methacrylate is used. The polymer powder composition may also contain a polymerization accelerator, or catalyst, which is designed to work in conjunction with the accelerator found in the polymerizable composition. Most preferred is a peroxide, such as benzoyl peroxide. The polymer powder may also contain other ingredients such as titanium dioxide and other dyes and/or pigments.

The monomer composition may contain 0.001-5%, preferably 0.001-4%, or more preferably 0.005-3% by weight of a polymerization accelerator, or catalyst, which is preferably an aromatic or aliphatic tertiary amine. Suitable aliphatic or aromatic tertiary amines include those set forth on pages 1532-1534 of the C.T.F.A. Cosmetic Ingredient Dictionary and Handbook, Seventh Edition, 1997, which is hereby incorporated by reference. Preferred are aromatic tertiary amines such as N,N-di($C_{1-6}$) alkyl-p-toluidines such as N,N-dimethyl-p-toluidine, N,N-diethyl-p-toluidine; or N,N-di($C_{1-6}$) alkyl anilines such as N,N-dimethyl aniline. The preferred accelerator is N,N-dimethyl-p-toluidine. The amine polymerization accelerator acts as a catalyst in chain extension and/or cross-linking of the monomers in the monomer composition. In the case where the polymerizable composition is polymerized by chemical means in a liquid/powder system, the most commonly used accelerator is an amine, as mentioned above, in combination with an organic peroxide such as benzoyl peroxide. Generally, the amine accelerator is found in the monomer composition and the peroxide in the powdered composition which is mixed with the monomer composition to cause polymerization immediately prior to application of the composition to the nail, as discussed above.

Components Used in Nail Coatings of the Invention

Reactive Monomers, and/or Oligomers, and/or Polymers

An embodiment of the liquid composition comprises reactive monomers, and/or oligomers, and/or polymers which provide the polymerized composition increased adhesion. In certain embodiments, such reactive monomers, and/or oligomers, and/or polymers can include an ethylenically unsaturated reactant, for example, a (meth)acrylate. As it is known to persons of skill in the polymer arts, the term (meth)acrylate encompasses acrylates and/or methacrylates. According to an aspect, such reactive monomers, and/or oligomers, and/or polymers may be selected from the group consisting of hydroxypropyl methacrylate (HPMA), hydroxyethyl methacrylate (HEMA), Ethyl methacrylate (EMA), Tetrahydrofurfuryl Methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and mixtures thereof. According to an aspect, such reactive monomers, and/or oligomers, and/or polymers may possess acidic functionality. According to an aspect, the monomer, oligomer or polymer which provides the polymerized composition increased adhesiveness is present from about 0 to about 50 wt %.

The ethylenically unsaturated reactant may be mono-, di-, tri-, or poly-functional as regards the addition-polymerizable ethylenic bonds. A variety of ethylenically unsaturated reactants are suitable, so long as the reactants are capable of polymerization to yield a polymerized artificial nail structure upon exposure to the appropriate stimuli. Suitable ethylenically unsaturated reactants are disclosed in U.S. Pat. No. 6,818,207 which is incorporated by reference.

High-Molecular Weight (Meth)Acrylate Polymer or Copolymer

According to some embodiments, the nail coatings of the present embodiments may also include a high-molecular weight (meth)acrylate polymer or copolymer. While the compositions of the present embodiments can include acrylates, methacrylates are preferred because methacrylates are less likely to cause skin sensitization than acrylate formulas. The term '(meth)acrylate' as used herein, means methacrylate, acrylate, or mixtures thereof.

In some embodiments, the high-molecular weight (meth)acrylate polymer or copolymer is a copolymer of an alkyl methacrylate (AMA) and methacrylic acid (MAA). The alkyl group may be, for example, methyl, ethyl, propyl or butyl. According to an aspect, the monomers are present in the polymer in a ratio of 90 parts AMA to 10 parts MAA (90:10 AMA/MAA). According to an aspect, the MAA monomer fraction may vary from 0 to 100% i.e. the (meth)acrylate polymer or copolymer may be an alkyl methacrylate polymer. According to an aspect, the AMA-MAA copolymer has a AMA:MAA monomer ratio of about 50:50. According to an aspect, the AMA-MAA copolymer has a AMA:MAA monomer ratio of about 60:40. According to an aspect, the AMA-MAA copolymer has a AMA:MAA monomer ratio of about 80:20. According to an aspect, the AMA-MAA copolymer has a AMA:MAA monomer ratio of about 90:10. According to an aspect, the AMA-MAA copolymer has a AMA:MAA monomer ratio of about 95:5.

In some embodiments, the high-molecular weight (meth)acrylate polymer or copolymer is a copolymer of methyl methacrylate (MMA) and methacrylic acid (MAA). According to an aspect, the monomers are present in the polymer in a ratio of 90 parts MMA to 10 parts MAA (90:10 MMA:MAA). According to an aspect, the MAA monomer fraction may vary from 0 to 100%; i.e. the (meth)acrylate polymer or copolymer may be a methyl methacrylate polymer. According to an aspect, the MMA-MAA copolymer has a MMA:MAA monomer ratio of about 50:50. According to an aspect, the MMA-MAA copolymer has a MMA:MAA monomer ratio of about 60:40. According to an aspect, the MMA-MAA copolymer has a MMA:MAA monomer ratio of about 80:20. According to an aspect, the MMA-MAA copolymer has a MMA:MAA monomer ratio of about 90:10. According to an aspect, the MMA-MAA copolymer has a MMA:MAA monomer ratio of about 95:5.

In some embodiments, the high-molecular weight (meth)acrylate copolymer is a copolymer of butyl methacrylate (BMA) and methacrylic acid (MAA). According to an aspect, the monomers are present in the polymer in a ratio of 90 parts BMA to 10 parts MAA (90:10 BMA:MAA). According to an aspect, the MAA monomer fraction may vary from 0 to 100% i.e. the (meth)acrylate polymer or copolymer may be a butyl methacrylate polymer. According to an aspect, the BMA-MAA copolymer has a BMA:MAA monomer ratio of about 50:50. According to an aspect, the BMA-MAA copolymer has a BMA:MAA monomer ratio of about 60:40. According to an aspect, the BMA-MAA copolymer has a BMA:MAA monomer ratio of about 80:20. According to an aspect, the BMA-MAA copolymer has a BMA:MAA monomer ratio of about 90:10. According to an aspect, the BMA-MAA copolymer has a BMA:MAA monomer ratio of about 95:5.

In some embodiments, the high-molecular weight (meth)acrylate polymer or copolymer has a molecular weight between 1,000 g/mol and 20,000 g/mol. In some embodiments, the high-molecular weight (meth)acrylate polymer or copolymer has a molecular weight of at least 2,000 g/mol. In some embodiments, the high-molecular weight (meth)acrylate polymer or copolymer has a molecular weight of at least 3,000 g/mol.

In some embodiments, the high-molecular weight (meth)acrylate polymer or copolymer has a molecular weight between 2,000 g/mol and 10,000 g/mol.

In some embodiments, the high-molecular weight (meth)acrylate polymer or copolymer has a molecular weight between 3,000 g/mol and 10,000 g/mol.

Urethane (Meth)Acrylate Resin

According to some embodiments, the nail coatings of the present embodiments may also include a urethane (meth)acrylate resin. While the compositions of the present embodiments can include urethane acrylates, urethane methacrylates are preferred because urethane methacrylates are less likely to cause skin sensitization than acrylate formulas. The term 'urethane (meth)acrylate' as used herein, means urethane methacrylate, urethane acrylate, or mixtures thereof.

In some embodiments, the urethane (meth)acrylates have a molecular weight between 200 g/mol and 20,000 g/mol. In some embodiments, the urethane (meth)acrylates have a molecular weight of at least 2,000 g/mol. In some embodiments, urethane (meth)acrylates have a molecular weight of at least 3,000 g/mol. In some embodiments, the urethane (meth)acrylates have a molecular weight between 2,000 g/mol and 10,000 g/mol. In some embodiments, the urethane (meth)acrylates have a molecular weight between 3,000 g/mol and 10,000 g/mol.

In some embodiments, the urethane (meth)acrylate is an aliphatic polyol modified urethane methacrylate. Such molecules may be formed by reaction of reactants comprising an aliphatic polyol, a hydroxyalkyl methacrylate, and a diisocyanate, and having a weight average molecular weight ($M_W$) ranging from, for example, about 1000 to about 6000. Methods for making polyol modified urethane methacrylate without the use of diisocyanate are also known. In some embodiments, the aliphatic polyol is a polyether, polyester, polybutadiene, and/or polycarbonate.

For example, in some embodiments, the urethane (meth)acrylate is a an aliphatic polyesterpolyol based urethane methacrylate. Such molecules may be formed by reaction of reactants comprising an aliphatic polyesterpolyol, a hydroxyalkyl methacrylate, and a diisocyanate, and having a weight average molecular weight ranging from, for example, about 1000 to about 6000.

In some embodiments, the hydroxyalkyl methacrylate is selected from the group consisting of hydroxymethyl methacrylate, hydroxyethyl methacrylate, hydroxyproyl methacrylate, hydroxybutyl methacrylate, hydroxypentyl methacrylate, hydroxyhexyl methacrylate, and combinations thereof, and more preferably, the hydroxyalkyl methacrylate is hydroxyethyl methacrylate.

In some embodiments, the diisocyanate is selected from the group consisting of isophorone diisocyanate (IPDI), dicyclohexylmethane diisocyanate, 1-methylcyclohexane-2, 4-diisocyanate, dicyclohexyl dimethyl-methane p,p'-diisocyanate, and combinations thereof. More preferably, the diisocyanate is isophorone diisocyanate.

In some embodiments, the urethane (meth)acrylate can be a polyester, polyether, polybutadiene and/or polycarbonate urethane oligomer (meth)acrylate.

In some embodiments, the urethane (meth)acrylate is a polyether urethane oligomer (meth)acrylate. By polyether urethane oligomer (meth)acrylate is meant a compound for example which contains at least polyether, urethane and (meth)acrylate groupings.

In some embodiments, the urethane (meth)acrylate is a polyester urethane oligomer (meth)acrylate. By polyester urethane oligomer (meth)acrylate is meant a compound, for example, which contains at least polyester, urethane and (meth)acrylate groups.

In some embodiments, the urethane (meth)acrylate is a polybutadiene urethane oligomer (meth)acrylate. By polybutadiene, urethane oligomer (meth)acrylate is meant a compound, for example, which contains at least polybutadiene, urethane and (meth)acrylate groups.

In some embodiments, the urethane (meth)acrylate is a polycarbonate urethane oligomer (meth)acrylate. By polycarbonate, urethane oligomer (meth)acrylate is meant a compound, for example, which contains at least polycarbonate, urethane and (meth)acrylate groups.

These urethane oligomer (meth)acrylates are accessible, in that a polyester, polyether, polybutadiene and/or polycarbonate diol (diol component) with an aliphatic, cycloaliphatic and/or aromatic diisocyanate, for example 1,6-hexamethylene diisocyanate (HDI), 2,4,4-trimethylhexamethylene-1,6-diisocyanate (TMDI), tetramethylene diisocyanate, isophorone diisocyanate, 4,4'-dicyclohexylmethane diisocyanate, 1,4-phenylene diisocyanate, 2,6- and 2,4-toluene diisocyanate, 1,5-naphthylene diisocyanate, 2,4'- and 4,4'-diphenylmethane diisocyanate (diisocyanate component) are reacted under amine or tin catalysis. If a molar excess of diol component compared with diisocyanate component is hereby used, terminal OH groups remain which can be esterified with an ethylenically unsaturated acid such as acrylic acid or methacrylic acid or one of their derivatives. If a molar excess of diisocyanate component compared with diol component is used, terminal isocyanate groups remain which are reacted with a hydroxyalkyl and/or hydroxyaryl (meth)acrylate and/or di(meth)acrylate and/or tri(meth)acrylate, such as for example 2-hydroxyethyl acrylate (HEA), 2-hydroxyethyl methacrylate (HEMA), 3-hydroxypropyl methacrylate (HPMA), 3-hydroxypropyl acrylate (HPA), glycerol dimethacrylate and/or glycerol diacrylate.

Usable polycarbonate polyols are, for example, products which result from reaction with diols, such as 1,3-propanediol, 1,4-butanediol, 1,6-hexanediol, diethylene glycol, neopentyl glycol, trimethyl-1,6-hexanediol, 3-methyl-1,5-pentanediol and/or tetraethylene glycol, with diaryl carbonates such as diphenyl carbonate, or with phosgene.

Usable polyether polyols include for example products which are accessible by polymerization of a cyclic oxide, for example ethylene oxide, propylene oxide or tetrahydrofuran or by addition of one or more of these oxides to polyfunctional initiators such as water, ethylene glycol, propylene glycol, diethylene glycol, cyclohexane dimethanol, glycerol, trimethylol propane, pentaerythrite or Bisphenol A. Particularly suitable polyether polyols are polyoxypropylene diols and triols, poly(oxyethylene-oxypropylene) diols and triols which are obtained by simultaneous or sequential addition of ethylene and propylene oxide to suitable initiators, as well as polytetramethylene ether glycols, which result from polymerization of tetrahydrofuran.

In some embodiments, polyethers include polyethylene oxide, polypropylene oxide, polybutylene oxide.

In some embodiments, polyesters include polypropylene glycol, polyethylene glycol, polytetramethylene glycol, ethylene oxide-propylene oxide copolymer, tetrahydrofuran-ethylene oxide copolymer, tetrahydrofuran-propylene oxide copolymer, terephthalic acid, isophthalic acid, naphthalenedicarboxylic acid, cyclohexanedicarboxylic, 1,2-propane diol (propylene glycol), dipropylene glycol, diethylene glycol, 1,3-butanediol, ethylene glycol, and glycerol.

Polymer which Conveys Enhanced Adhesiveness and which Confers Solvent Sensitivity to the Polymerized Lattice Certain embodiments of the liquid composition comprise at least one polymer which is incorporated within the 3-D lattice and which conveys enhanced adhesiveness and which confers solvent sensitivity to the polymerized lattice. The presence of certain polymers at the polymer/nail interface renders the interfacial bonds susceptible to rupture by organic solvents.

According to an aspect, a polymer which conveys both enhanced adhesion and which sensitizes the polymer/nail interface to solvent is a co-polymer of polymethyl methacrylate (PMMA) and polymethacrylic acid (PMAA). According to an aspect, the monomers are present in the polymer in a ratio of 90 parts PMMA to 10 parts PMAA (90:10 PMMA:PMAA). According to an aspect, the PMAA monomer fraction may vary from 0 to 100%. According to an aspect, the PMMA-PMAA copolymer has a PMMA:PMAA monomer ratio of about 50:50. According to an aspect, the PMMA-PMAA copolymer has a PMMA:PMAA monomer ratio of about 60:40. According to an aspect, the PMMA-PMAA copolymer has a PMMA:PMAA monomer ratio of about 80:20. According to an aspect, the PMMA-PMAA copolymer has a PMMA:PMAA monomer ratio of about 90:10. According to an aspect, the PMMA-PMAA copolymer has a PMMA:PMAA monomer ratio of about 95:5.

Certain embodiments of the liquid composition comprise at least one monomer which imparts to the interfacial bonds a high degree of sensitivity to organic solvent. According to an aspect, the at least one monomer may be polypropylene glycol-4-monomethacrylate (PPG-4 monomethacrylate) or polypropylene glycol-5-monomethacrylate (PPG-5 monomethacrylate). According to an aspect, suitable monomers may include any acrylated or methacrylated monomer in the polyethylene glycol (PEG), polypropylene glycol (PPG), or polybutylene glycol (PBG) families. According to an aspect, such monomers are present at from about 0 to about 70 weight % (wt %).

In certain embodiments, the monomer that imparts to the interfacial bonds a high degree of sensitivity to organic solvent may be a polyol modified urethane (meth)acrylate.

In certain embodiments, the removable, adhesion-promoting nail coating composition further comprises monomers and oligomers chosen such that various bonds within the resulting thermoset are provided an increased sensitivity to solvent. In certain embodiments, such monomers and oligomers are selected from the group consisting of propoxylated allyl methacrylate, methoxy polyethylene glycol (350) monomethacrylate, polyethylene glycol (600) monomethacrylate, stearyl methacrylate, tridecyl methacrylate, hydroxyethyl methacrylate acetate, and mixtures thereof.

Urethane (Mmeth)Acrylate Resin

Certain embodiments of the polymerizable liquid composition of the present disclosure may comprise a urethane (meth)acrylate resin which may convey flexibility and toughness to the polymerized product. In certain embodiments, urethane methacrylates are preferred. The urethane (meth)acrylate monomer may be present from about 0 to about 80 wt %. In certain embodiments, the urethane (meth) acrylate may have a molecular weight (grams/mole) of from about 100 to about 20,000. In certain embodiments, the urethane (meth)acrylate may have a molecular weight of from about 300 to about 15,000. In certain embodiments, the urethane (meth)acrylate may have a molecular weight of from about 500 to about 13,000. In certain embodiments, the urethane (meth)acrylate may have a molecular weight of from about 500 to about 6,000.

A (Meth)Acrylate Monomer which Provides Improved Adhesion, Viscosity, Wear and Durability An embodiment of the present disclosure provides a polymerizable liquid composition comprised of a (meth) acrylate monomer which provides improved adhesion, viscosity, wear and durability. In certain embodiments, the (meth)acrylate monomer is a tetrahydrofurfuryl methacrylate. In other embodiments, some or all of the tetrahydrofurfuryl methacrylate may be substituted by such monomers including, but not limited to methyl or ethyl methacrylate, hydroxypropyl or hydroxybutyl methacrylate, and/or other monomers such as pyromellitic dianhydride glyceryl dimethacrylate, and similar (meth)acrylate monomers. The aromatic or aliphatic (meth)acrylate monomer may be present from about 0 to about 70 wt %.

Aromatic or Aliphatic (Meth)Acrylate Monomer which may be Present to Improve Adhesion Certain embodiments of the present disclosure may comprise other aromatic or aliphatic (meth)acrylate monomers which may be present to improve adhesion. The (meth) acrylate monomer may be a pyromellitic dianhydride glyceryl dimethacrylate (PMGDM). In general, this methacrylate monomer may be an acid-functional, (meth)acrylate monomer. The acid-functional, (meth)acrylate monomer may be a carboxylic acid polymer. This methacrylate monomer may be present from about 0 to about 70 wt %.

Free Hydroxyl Groups

The inventive composition comprises monomers and oligomers having a plurality of free hydroxyl groups. The hydroxyl groups of the inventive composition may be available to form hydrogen bonds with a substrate which may be a keratinous nail surface. The hydroxyl groups of the inventive composition may be available to form hydrogen bonds with a substrate which may be a surface of a natural nail or artificial nail enhancement coating.

Adhesion Promoter (Other than POSS)

Certain embodiments of the removable, adhesion-promoting nail coating composition may comprise an adhesion promoter in addition to POSS. The additional adhesion promoter can be selected from the group consisting of hydroxypropyl methacrylate (HPMA), hydroxyethyl methacrylate (HEMA), ethyl methacrylate (EMA), tetrahydrofurfuryl methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, methacroyloxyethyl maleate, 2-hydroxyethyl methacrylate/succinate, 1,3-glycerol dimethacrylate/succinate adduct, butyl methacrylate, isobutyl methacrylate, Polyethylene glycol-4 (PEG-4) dimethacrylate, Polypropylene Gylcol (PPG) monomethacrylate, trimethylolpropane trimethacrylate, isopropylidenediphenyl bisglycidyl methacrylate, lauryl methacrylate, cyclohexyl methacrylate, hexyl methacrylate, urethane methacrylate, triethylene glycol dimethacrylate, ethylene glycol dimethacrylate, tetraethylene glycol dimethacrylate, trimethylolpropane trimethacrylate, neopentylglycol dimethacylate, acetoacetoxy methacrylate, acetoacetoxyethyl methacrylate (AAEMA), polyetheramine, glycidyl methacrylates, maleic anhydride, terpolymers containing vinyl acetate, organosilanes, organotitanates, chlorinated polyolefins, sucrose acetate isobutyrate, caprylic/capric triglyceride, glyceryl hydrogenated rosinate, pentaerythryl hydrogenated rosinate, styrene/methyl styrene/indene copolymer, blocked isocyanate Polyvinyl Chloride (PVC), polyamidoamine PVC, and mixtures thereof.

Non-Reactive, Solvent-Dissolvable Polymer (Film-Former)

Certain embodiments of the polymerizable liquid composition of the present disclosure may comprise a non-reactive, solvent-dissolvable polymer. According to an aspect, the non-reactive, solvent-dissolvable polymer is a cellulose ester. According to a particular aspect, the non-reactive, solvent-dissolvable polymer is a cellulose acetate alkylate. According to a more particular aspect, the non-reactive, solvent-dissolvable polymer is a cellulose acetate butyrate or a cellulose acetate propionate. The non-reactive, solvent-dissolvable polymer may be a mixture of any acceptable polymer. According to a further aspect, the non-reactive, solvent-dissolvable polymer may be present at from about 0 to about 75 wt %.

The removable, adhesion-promoting nail coating composition may comprise a non-reactive, solvent-dissolvable polymer selected from the group consisting of ethyl tosylamide, adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, poly lactic acid, nitrocellulose, cellulose ester, and mixtures thereof Optional Resin(s)

Certain embodiments of the formulation may optionally comprise resins, such as, but not limited to polyvinylbutyral and/or tosylamide formaldehyde resins. Such resins may act as film formers, adhesion promoters, and aids to removal. These resins may also qualify as solvent-dissolvable resins which are dispersed in the polymerized structure and can be easily dissolved by a solvent to facilitate solvent absorption and migration during removal.

Plasticizers

The compositions of the invention may contain from about 0.001 wt % to about 20 wt % of a plasticizer. The compositions of the invention may contain from about 0.01 wt % to about 15 wt %, from about 0.05 wt % to about 10 wt %, from about 0.1 wt % to about 5 wt %, or from about 0.5 wt % to about 2 wt % of a plasticizer. The plasticizer causes the polymerized nail structure to have improved flexibility and reduced brittleness. Suitable plasticizers may be esters, low volatility solvents, or non-ionic materials such as nonionic organic surfactants or silicones.

In certain embodiments, the removable, adhesion-promoting nail coating composition further comprises from about 0.001 wt % to about 20 wt %, from about 0.01 wt % to about 15 wt %, from about 0.05 wt % to about 10 wt %, from about 0.1 wt % to about 5 wt %, or from about 0.5 wt % to about 2 wt % of a plasticizer selected from the group consisting of esters, low volatility solvents (paraffinic hydrocarbons, butyrolactone, xylene, methyl isobutyl ketone), non-ionic surfactants, non-ionic silicones, isostearyl isononanoate, silicones, diisobutyl adipate, trimethyl pentanyl diisobutyrate, acetyl tributyl citrate, and mixtures thereof.

Suitable esters include those having the general structure RCO—OR' where RCO— represents a carboxylic acid radical and where —OR' is an alcohol residue. Preferably R and R' are fatty radicals, having 6 to 30 carbon atoms, and may be saturated or unsaturated. Examples of suitable esters are those set forth on pages 1558 to 1564 of the C.T.F.A. Cosmetic Ingredient Dictionary and Handbook, Seventh Edition, 1997, which is hereby incorporated by reference. In the preferred compositions of the invention, the plasticizer is an ester of the formula RCO—OR' wherein R and R' are each independently a straight or branched chain $C_{6-30}$ alkyl. A suitable plasticizer is isostearyl isononanoate. Other suitable plasticizers are disclosed in U.S. Pat. No. 6,818,207 which is incorporated by reference UV Stabilizing Agent According to certain embodiments, the formulations may further comprise at least one UV stabilizing agent. In certain embodiments, the UV stabilizer is present at up to 2 wt %.

The compositions of the invention may contain one or more UV absorbers, which assist in reducing the yellowing which is often seen in artificial nails. UV absorbers have the ability to convert incident UV radiation into less damaging infrared radiation (heat), or visible light. A recommended amount of UV absorber is 0.001-5% by weight of the total composition. Suitable UV absorbers include hydroxy benzotriazole compounds and benzophenone compounds such as are disclosed in U.S. Pat. No. 6,818,207, incorporated by reference.

The removable, adhesion-promoting nail coating composition may comprise up to 5 wt % of a UV-absorber selected from the group consisting of hydroxy benzotriazole compounds such as 2-(2-hydroxy-5'-methylphenyl)benzotriazole, benzophenones, 1-12, 3-benzylidene camphor, benzyl salicylate, borneolone, borneol, camphor, bumetrizole, Para-amino benzoic acid (PABA), butyl PABA, butyl methoxydibenzoylmethane, cinoxate, Diethanolamine (DEA)-methoxycinnamate, dibenzoxazoyl naphthalene, digalloyl trioleate, diisopropyl methyl cinnamate compounds sold under the trademark TINUVIN® and mixtures thereof.

Polymerization/Photoinitiator

Certain embodiments of the disclosed polymerizable composition may be viscous gels or liquids. Gel or liquid embodiments may be polymerized by exposure to radiant energy, such as heat, visible, UV, or electron-beam radiation. Liquid or gel embodiments are applied upon nails and may be shaped to the desired configuration. The coated nails are exposed to a polymerization initiator, for example radiant energy or a chemical polymerization initiator such as a peroxide is included or mixed into the formulation, and polymerization occurs.

The inventive composition may be polymerizable with actinic radiation. The actinic radiation may be visible, ultraviolet (UV), or electron beam radiation. The UV radiation may be characterized by a wavelength, or group of wavelengths, typically, but not limited to about 320 to about 420 nanometers.

After the liquid composition is applied to a nail surface, the liquid is polymerized or cured. The liquid composition comprises ethylenically unsaturated (meth)acrylates which may be polymerized or cured by a UV-initiated, free-radical polymerization method. Persons of skill in the polymerization arts may readily determine suitable photoinitiators for use with the invention. Suitable photoinitiators include, but are not limited to benzoyldiphenylsphosphinates, phenyl ketones, and dimethyl ketals. Set forth below are non-limiting representative photoinitiators that are suitable for purposes of the invention.

A non-limiting suitable photoinitiator is a 2,4,6-trimethylbenzoyldiphenylphosphorous derivative. A suitable derivative is ethyl-2,4,6-trimethylbenzoyldiphenylphosphinate, sold under the trademark LUCIRIN® TPO-L (BASF Aktiengesellschaft, Ludwigshafen, DE). Another non-limiting suitable derivative is 2,4,6-trimethylbenzoyldiphenylphosphine oxide, sold under the trademark LUCERIN® (BASF) or as Genocure GENOCURE®TPO (Rahn). The 2,4,6-trimethylbenzoyldiphenylphosphinate photoinitiator may be present from about 0% to about 20 wt %.

A non-limiting suitable photoinitiator is hydroxycyclohexyl phenyl ketone, sold under the trademark IRGACURE® 184 and which may be present from about 0 to about 20 wt %.

A non-limiting suitable photoinitiator is benzil dimethyl ketal (BDK), sold under the trademark FIRSTCURE® BDK (Albemarle, Baton Rouge, La., US) and which may be present from about 0 to about 20 wt %.

Polymerization Regulators

It may be desirable to include one or more polymerization regulators. A polymerization regulator assists in preventing the polymerization of the monomer composition from occurring too quickly. Hydroquinone and similar materials are suitable polymerization regulators. Suggested ranges of polymerization regulators are from about 0.0001-5% by weight of the total composition. Suitable polymerization regulators are disclosed in U.S. Pat. No. 6,818,207, incorporated by reference.

Color Layer/Color Agents

An aspect of the disclosure provides a color layer. Certain embodiments of a color layer may comprise up to 10 wt % pigments and/or dyes. Embodiments of the basecoat and topcoat may have up to 1 wt % pigments and/or dyes. High concentrations of pigments and/or dyes may absorb UV radiation. To compensate therefore, certain embodiments of the present disclosure may comprise higher concentrations, up to 20 wt %. photoinitiator.

Solvents

A conventional thermoset nail coating comprises 100% solids and does not comprise non-reactive solvents. The polymerizable liquid composition of the present disclosure further comprises at least one non-reactive solvent. A suitable non-reactive solvent is readily volatile at room temperature and is a good solvent for the remaining ingredients. Upon application, the non-reactive solvent readily volatilizes leaving regions of increased porosity throughout the nail coating. These porous regions later facilitate the entry of a remover solvent which may be acetone.

Suitable non-reactive solvents may be selected from the group consisting of ketones, alkyl acetates, alcohols, alkanes, alkenes, and mixtures thereof. Suitable solvents may be selected from the group consisting of acetone, ethyl acetate, butyl acetate, isopropyl alcohol, ethanol, methyl ethyl ketone, toluene, hexane, and mixtures thereof. A particularly suitable solvent is acetone. Typically a solvent or a mixture of solvents is included at up to about 70 weight percent.

EXAMPLES

It is understood that modifications which do not substantially affect the activity of the various embodiments of this invention are also provided within the definition of the invention provided herein. Accordingly, the following examples are intended to illustrate but not limit the present invention. While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

Example 1

In one example, a basecoat nail coating composition can have the following components:

| | Wt. % | |
| --- | --- | --- |
| Component | Clear Base Formula A | Clear Base Formula B |
| Ethyl Acetate | 50.340 | 40.1000 |
| Butyl Acetate | 15.592 | 24.2499 |
| Phthalic Anhydride/Trimellitic Anhydride/Glycols Copolymer | 11.508 | |

-continued

| | Wt. % | |
| --- | --- | --- |
| Component | Clear Base Formula A | Clear Base Formula B |
| Adipic Acid/Neopentyl Glycol/Trimellitic Copolymer | | 7.2000 |
| Nitrocellulose | 11.389 | 13.0000 |
| Cellulose Acetate Butyrate | | |
| Acetyl Tributyl Citrate | 6.290 | 5.6000 |
| IPA | 4.881 | 5.6000 |
| Acrylates Copolymer | | |
| Heptane | | 4.0000 |
| Violet 2 CI60725 | 0.001 | 0.0001 |
| Benzophenone | | 0.2000 |
| Trimethylpentanediyl dibenzoate | | 0.0500 |

Exemplary clear nail coatings according to the above formulations, plus added POSS, were prepared, tested and compared to control samples (without added POSS). Control samples correspond to a commercially available clear nail enamel.

| Formula # | EP0409 | Acetyl Tributyl Citrate | Clear Base Formula A | Clear Base Formula B |
| --- | --- | --- | --- | --- |
| 1 | 2 | 2 | | 96 |
| 1 Control | 0 | 0 | | 100 |
| 2 | 2 | 2 | 96 | |
| 2 Control | 0 | 0 | 100 | |

The above compositions were tested for adhesion using the Cross Hatch Adhesion test (ASTM D3359). Briefly, a crosshatch pattern is made though the film to the substrate. Detached flakes of coating are removed by brushing with a soft brush. Pressure-sensitive tape is applied over the crosshatch cut. Tape is smoothed into place by using a pencil eraser over the area of the incisions. Tape is removed by pulling it off rapidly back over itself as close to an angle of 180°. Adhesion is assessed on a 0 to 5 scale. The table below summarizes the results from testing.

| FORMULA # | AVERAGE ADHESION SCORE | Improvement over Control |
| --- | --- | --- |
| 1 | 3.0 | 71% |
| 1 Control | 1.75 | — |
| 2 | 2.25 | 125% |
| 2 Control | 1.0 | — |

Adhesion was measured for this formulation, and for the same formulation with varying amounts of POSS EP0409 added.

| POSS | Avg. Adhesion Score |
| --- | --- |
| 0 wt % | 3.17 |
| 2 wt % EP0409 | 3.67 |
| 4.67 wt % EP0409 | 4.25 |
| 10 wt % EP0409 | 4.50 |

Example 2

In another exemplary embodiment, a basecoat nail coating composition to which POSS can advantageously be added has the following components:

| Ingredient | Exemplary formula |
| --- | --- |
| Tetrahydrofurfuryl Methacrylate | 20.04600 |
| PPG-5 Methacrylate | 20.04600 |
| Cellulose Acetate Butyrate | 16.06700 |
| Acetone | 12.50971 |
| Bis-HEMA Poly(1,4-Butanediol)-22/IPDI Copolymer | 11.43600 |
| Alcohol Denat. | 4.59821 |
| Acrylates Copolymer | 4.52958 |
| Di-HEMA Trimethylhexyl Dicarbamate | 4.35000 |
| Hydroxycyclohexyl Phenyl Ketone | 2.11020 |
| Butyl Acetate | 1.40680 |
| Ethyl Trimethylbenzoyl Phenylphosphinate | 1.40000 |
| Bis(Glyceryl Dimethacrylate) Pyromellitate | 0.55850 |
| Phenyldimethoxyacetophenone | 0.23550 |
| Hydroxypropyl Methacrylate | 0.70650 |
| | 100.00000 |

Example 3

Adhesion was measured for a basecoat composition including a color agent, HEMA, HPMA, Di-HEMA trimethylhexyl carbamate, and hydroxycyclohexyl phenyl ketone, and for the same formulation with a 1:1 mixture of ethyl acetate:POSS added to give 10 wt % POSS in the final formulation:

| POSS | Avg. Adhesion Score |
| --- | --- |
| 0% | 1.67 |
| 10 wt % EP0409 | 4.17 |
| 10 wt % AM0281 | 4.00 |
| 10 wt % NB1038 | 4.83 |
| 10 wt % PM1285MV | 2.17 |

Example 5

Adhesion was measured for a basecoat formulation including the following components: a color agent, HEMA, HPMA, Isobornyl methacrylate, Di HEMA trimethylhexyl carbamate, Benzophenone, Hydroxycylcohexyl Phenyl Ketone, TPO, Trimethyl Pentaryl Diisobutyrate, Camphor, Dimethicone, Nitrocellulose, Tosylamide/Epoxy Resin, Polyvinyl butyral, Butyl Acetate, Alcohol, and Heptane. Adhesion was measured for the formulation, and for the same formulation with a 1:1 mixture of ethyl acetate:POSS added to give 10 wt % POSS in the final formulation.

| POSS | Avg. Adhesion Score |
| --- | --- |
| 0 wt % | 3.83 |
| 10 wt % EP0408 | 3.83 |
| 10 wt % AM0281 | 4.00 |
| 10 wt % NB1038 | 4.00 |

Example 6

Adhesion was measured for the basecoat formulation of Example 5, and for the same formulation with a 1:1 mixture of HEMA:POSS added to give 10 wt % POSS in the final formulation.

| POSS | Avg. Adhesion Score |
| --- | --- |
| 0% | 3.83 |
| 10 wt % PM1258MV | 4.50 |

Example 7

In one exemplary embodiment, a color layer nail coating composition to which POSS may be advantageously added has the following components:

| Ingredient | Exemplary formula | Possible Range |
| --- | --- | --- |
| Butyl Acetate | 24.00000 | >10-30% |
| Bis-HEMA Poly(1,4-Butanediol)-22/IPDI Copolymer | 14.02000 | >10-30% |
| Cellulose Acetate Butyrate | 18.83660 | >10-30% |
| PPG-5 Methacrylate | 12.81000 | >10-30% |
| Tetrahydrofurfuryl Methacrylate | 12.81000 | >10-30% |
| Di-HEMA Trimethylhexyl Dicarbamate | 3.00000 | >3-10% |
| Phenyldimethoxyacetophenone | 0.40000 | >1-3% |
| Hydroxypropyl Methacrylate | 1.42000 | >1-3% |
| Silica | 0.50000 | >.3-1% |
| MAY CONTAIN THESE INGREDIENTS: | | |
| Titanium Dioxide | | >3-10% |
| Mica | | >3-10% |
| Hydroxycyclohexyl Phenyl Ketone | 4.20000 | >3-10% |
| Ethyl Trimethylbenzoyl Phenylphosphinate | | >3-10% |
| Trimethylbenzoyl Diphenylphosphine Oxide | 2.00000 | >1-3% |
| Methyl Pyrrolidone | | >.1-.3% |
| Isopropyl Alcohol | | >.3-1% |
| Nitrocellulose | | >.3-1% |
| Tin Oxide | | >.1-.3% |
| Stearalkonium Hectorite | | <.1% |
| Drometrizole | 0.00330 | <.1% |
| MAY CONTAIN THESE COLORANTS: | | |
| CI 15850 (Red 6 Lake) | | >.3-1% |
| CI 15850 (Red 7 Lake) | | >.3-1% |
| CI 15880 (Red 34 Lake) | | >.1-.3% |
| CI 19140 (Yellow 5 Lake) | | >1-3% |
| CI 60730 (Ext. Violet 2) | 0.00010 | <.1% |
| CI 77163 (Bismuth Oxychloride) | | >3-10% |
| CI 77491 (Iron Oxides) | | >1-3% |
| CI 77499 (Iron Oxides) | | >1-3% |
| CI 77891 (Titanium Dioxide) | 6.00000 | >3-10% |

Example 8

Adhesion was measured for a color layer formulation of Example 7, and for the same formulation with 10 wt % of POSS NB1038. The first set of tests (left column) was with 1 coat, 4 min cure, IPA wipe. The second set (right column) was with 2 coats, 4 min cure, IPA wipe.

| POSS additive | Average Adhesion Score | |
| --- | --- | --- |
| 0% | 1.33 | 0.50 |
| 10 wt % NB1038 | 3.50 | 3.83 |

Example 9

Adhesion was measured for a color layer formulation including the following components: Stearalkonium Hectorite, Color, HEMA, HPMA, Isobornyl methacrylate, Di HEMA trimethylhexyl carbamate, Hydroxycyclohexyl Phenyl Ketone, Citric Acid, Dimethicone (Plasticizer), Phosphoric Acid, Nitrocellulose, Butyl Acetate, Diacetone Alcohol, and Ethyl Acetate, and for the same formulation with a 1:1 mixture of ethyl acetate:POSS added to give 10 wt % POSS in the final formulation.

| POSS | Average Adhesion Score |
|---|---|
| 0% | 0.00 |
| 10 wt % NB1038 | 0.50 |
| 10 wt % AM0281 | 0.50 |

Example 10

Adhesion was measured for a color layer formulation including the following components: Colorant, HEMA, HPMA, Di HEMA trimethylhexyl carbamate, Benzophenone-1, Diphenyl-2,4-trimethylbenzoyl phosphinic acid, Dimethicone, Polysilicone-13, PEG-2 Dimethicone, and Synthetic Wax, and for the same formulation with a 1:1 mixture of HEMA:POSS, or a 1:1 mixture of THFMA:POSS, added to give 10 wt % POSS in the final formulation.

| POSS | Avg. Adhesion Score |
|---|---|
| 0% | 0.83 |
| 10 wt % NB1038/THFMA | 2.83 |

Example 11

Peak strength and peel strength of a liquid-and-powder nail coating was measured by Hesiometer analysis. Samples were tested on a Romulus IIIA Hesiometer. Test method was set so each test allowed for 4.5 mm of travel with the blade set at 15° angle while applying 10 Newtons of force to the substrate. Data was derived from a plot of force vs. displacement. To determine the data point for the peak or impact strength, the integral of the initial data peak was taken. To determine the data point for Peel or Adhesive Strength the, the integral of the plateau from 2.5 mm to 4.5 mm was taken.

|  | Liquid-and-Powder | | Liquid with 5% POSS + Powder | |
|---|---|---|---|---|
|  | Peak Strength | Peel Strength | Peak Strength | Peel Strength |
| Ave. | 219.6 | 159.25 | 1064.78 | 121.53 |
| Std. Dev. | 18.9 | 15.15 | 126.16 | 7.84 |
| % SDev. | 8.60 | 9.51 | 11.84 | 6.45 |

The tests performed showed a great increase of Peak or Impact strength with the addition of the Glycidyl POSS. After examination of the samples, the reduction of Peel strength may be a result of a delamination of the coating ahead of the blade due to the amount of force exerted during the Peak Strength measurement which can affect the peel strength measurement.

Example 12

Adhesion was measured for a series of water-based enamels, and for the same formulations with added POSS (EP0409). The water-based enamel used was a commercially available product that includes water, a styrene acrylates copolymer emulsion, an acrylate copolymer emulsion and colorants. The POSS was added directly to these formulations at levels of 1% and 5%.

| POSS | Average Dry Adhesion Score | Average Wet Adhesion Score |
|---|---|---|
| 0% | 2.5 | 0.17 |
| 1% POSS | 4.25 | 1.33 |
| 5% POSS | 3.67 | 1.50 |

Other embodiments are within the scope of the following claims.

What is claimed is:

1. A method of improving adhesion of a nail coating comprising:
providing a nail coating composition comprising at least one reactive monomer, oligomer or polymer selected from the group consisting of reactive (meth)acrylates and mixture thereof;
adding at least one polyhedral oligomeric silsesquioxane to the nail coating composition, wherein the at least one polyhedral oligomeric silsesquioxane has the formula $(C_6H_{11}O_2)_n(SiO_{1.5})_n$, where n is 8, 10, or 12, and wherein $(C_6H_{11}O_2)$ represents:

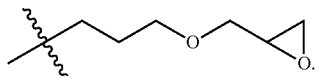 [SMILES: *CCCOCC1CO1]

2. The method of claim 1, wherein the at least one reactive monomer, oligomer or polymer is a reactive (meth)acrylate.

3. The method of claim 2, wherein the reactive (meth)acrylate is selected from the group consisting of hydroxypropyl methacrylate, hydroxyethyl methacrylate, ethyl methacrylate, tetrahydrofurfuryl methacrylate, pyromellitic dianhydride di(meth)acrylate, pyromellitic dianhydride glyceryl di methacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, and a mixture thereof.

4. The method of claim 1, wherein the nail coating composition further comprises a film-forming polymer or a non-reactive solvent-dissolvable polymer.

5. The method of claim 4, wherein the non-reactive, solvent-dissolvable polymer or film-forming polymer is selected from the group consisting of a cellulose ester, a cellulose acetate alkylate, a cellulose acetate butyrate, a cellulose acetate propionate, adipic acid/fumaric acid/phthalic acid/tricyclodecane dimethanol copolymer, adipic acid/neopentyl glycol/trimellitic anhydride copolymer, phthalic anhydride/trimellitic anhydride/glycols copolymer, polyethyl cellulose, polyhydroxypropyl cellulose, polyethyl acrylate oxide, polylactic acid, nitrocellulose, and mixtures thereof.

6. The method of claim 1, wherein the nail coating composition further comprises a high-molecular weight (meth)acrylate polymer or copolymer.

7. The method of claim 1, wherein the nail coating composition further comprises a polymethylmethacrylate-polymethylacrylic acid copolymer.

8. The method of claim 1, wherein the nail coating composition further comprises a solvent.

9. The method of claim 8, wherein the solvent is a non-aqueous solvent.

10. The method of claim 8, wherein the solvent is water.

11. The method of claim 1, wherein the nail coating composition further comprises a reactive polypropylene glycol (meth)acrylated monomer or a reactive polyethylene glycol (meth)acrylated monomer.

12. The method of claim 1, wherein the nail coating composition further comprises a polymerization accelerator, a polymerization initiator, or a combination thereof.

13. The method of claim 1, wherein the nail coating composition further comprises an adhesion promoter selected from the group consisting of hydroxypropyl methacrylate, hydroxyethyl methacrylate, ethyl methacrylate, tetrahydrofurfuryl methacrylate, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, methacroyloxyethyl maleate, 2-hydroxyethyl methacrylate/succinate, 1,3-glycerol dimethacrylate/succinate adduct, butyl methacrylate, isobutyl methacrylate, PEG-4 dimethacrylate, PPG monomethacrylate, trimethylolpropane trimethacrylate, isopropylidenediphenyl bisglycidyl methacrylate, lauryl methacrylate, cyclohexyl methacrylate, hexyl methacrylate, urethane methacrylate, triethylene glycol dimethacrylate, ethylene glycol dimethacrylate, tetraethylene glycol dimethacrylate, trimethylolpropane trimethacrylate, neopentylglycol dimethacylate, acetoacetoxy methacrylate, acetoacetoxyethyl methacrylate, polyetheramine, glycidyl methacrylates, maleic anhydride, terpolymers containing vinyl acetate, organosilanes, organotitanates, chlorinated polyolefins, sucrose acetate isobutyrate, caprylic/capric triglyceride, glyceryl hydrogenated rosinate, pentaerythryl hydrogenated rosinate, styrene/methyl styrene/indene copolymer, and a mixture thereof.

14. The method of claim 1, wherein the nail coating composition further comprises at least one non-reactive, solvent dissolvable polymer and the reactive monomer, oligomer or polymer is a reactive (meth)acrylate.

15. The method of claim 1, wherein the nail coating composition further comprises at least one polymethylmethacrylate-polymethylacrylic acid copolymer; at least one non-reactive, solvent dissolvable polymer; and at least one non-reactive solvent; and wherein the reactive monomer, oligomer or polymer is a reactive (meth)acrylate.

* * * * *